US011129777B2

(12) United States Patent
Verhovnik et al.

(10) Patent No.: US 11,129,777 B2
(45) Date of Patent: Sep. 28, 2021

(54) MICROCAPSULES WITH IMPROVED DEPOSITION

(71) Applicant: FIRMENICH SA, Satigny (CH)

(72) Inventors: Glenn Verhovnik, Satigny (CH); Arnaud Struillou, Satigny (CH); Daniel Reichlin, Bernex (CH)

(73) Assignee: Firmenich SA, Satigny (CH)

( * ) Notice: Subject to any disclaimer, the term of this patent is extended or adjusted under 35 U.S.C. 154(b) by 0 days.

(21) Appl. No.: 16/648,743

(22) PCT Filed: Nov. 14, 2018

(86) PCT No.: PCT/EP2018/081182
§ 371 (c)(1),
(2) Date: Mar. 19, 2020

(87) PCT Pub. No.: WO2019/096817
PCT Pub. Date: May 23, 2019

(65) Prior Publication Data
US 2020/0268623 A1 Aug. 27, 2020

(30) Foreign Application Priority Data
Nov. 15, 2017 (EP) .................................. 17201902

(51) Int. Cl.
| | | |
|---|---|---|
| *A61K 8/11* | (2006.01) | |
| *A61K 8/06* | (2006.01) | |
| *A61K 8/73* | (2006.01) | |
| *A61K 8/81* | (2006.01) | |
| *A61Q 5/02* | (2006.01) | |
| *A61Q 5/12* | (2006.01) | |
| *A61Q 19/10* | (2006.01) | |
| *B01J 13/14* | (2006.01) | |
| *B01J 13/22* | (2006.01) | |

(52) U.S. Cl.
CPC ............... *A61K 8/11* (2013.01); *A61K 8/062* (2013.01); *A61K 8/731* (2013.01); *A61K 8/737* (2013.01); *A61K 8/8158* (2013.01); *A61Q 5/02* (2013.01); *A61Q 5/12* (2013.01); *A61Q 19/10* (2013.01); *B01J 13/14* (2013.01); *B01J 13/22* (2013.01); *A61K 2800/412* (2013.01); *A61K 2800/56* (2013.01)

(58) Field of Classification Search
CPC ...... A61K 8/737; A61K 8/8158; A61K 8/731; A61K 8/11; A61K 8/062; A61K 2800/412; A61K 2800/56; A61Q 5/02; A61Q 5/12; A61Q 13/00; A61Q 19/02; A61Q 19/10; A01N 25/28; A23L 27/72; C11D 17/0039; C11D 3/505; B01J 13/16; B01J 13/14; B01J 13/22
See application file for complete search history.

(56) References Cited

U.S. PATENT DOCUMENTS

2006/0210509 A1   9/2006   Johnson et al.

FOREIGN PATENT DOCUMENTS

| WO | 2009153695 A1 | 12/2009 | |
|---|---|---|---|
| WO | 2013068255 A1 | 5/2013 | |
| WO | 2013092375 A1 | 6/2013 | |
| WO | 2015110568 A1 | 7/2015 | |
| WO | 2016116604 A1 | 7/2016 | |
| WO | WO-2016116604 A1 * | 7/2016 | ............ B01J 13/185 |
| WO | WO-2016193435 A1 * | 12/2016 | ............ A61Q 13/00 |
| WO | 2017001385 A1 | 1/2017 | |

OTHER PUBLICATIONS

International Search Report and Written Opinion for corresponding International Application No. PCT/EP2018/081182, dated Jan. 24, 2019, 3 pages.
Written Opinion of the International Searching Authority for corresponding International Application No. PCT/EP2018/081182, dated Jan. 24, 2019, 7 pages.

* cited by examiner

*Primary Examiner* — Blessing M Fubara
(74) *Attorney, Agent, or Firm* — Armstrong Teasdale LLP

(57) ABSTRACT

The present disclosure relates to microcapsules having an oil-based core and a polymeric shell coated with at least a cationic polymer. Microcapsules defined in the present disclosure combine the presence of an anionic emulsifier and a cationic polymer according to a specific charge density range to optimize the deposition in rinse-off applications.

20 Claims, No Drawings

MICROCAPSULES WITH IMPROVED DEPOSITION

CROSS-REFERENCE TO RELATED APPLICATIONS

This application is a U.S. National Phase application of PCT/EP2018/081182, filed Nov. 14, 2018, which claims priority to EP Application No. 17201902.8, filed on Nov. 15, 2017, the contents of which are hereby incorporated by reference in their entirety.

TECHNICAL FIELD

The present invention relates to the field of delivery systems. More specifically, the invention concerns microcapsules formed by interfacial polymerization, which have a particularly high rate of deposition when applied on a substrate and which can be advantageously used in several industries, in particular in the perfumery industry. Perfuming compositions and perfumed consumer products comprising these microcapsules are also objects of the invention.

BACKGROUND OF THE INVENTION

Delivery system, e.g. capsules containing a perfume, to release the fragrance in a controlled manner are commonly used in the perfumery industry and well documented in the art.

In order to be successfully used in consumer products, one of the issues faced is to provide delivery systems that are well deposited on the substrate for the treatment of which the end product is intended to be used, such as textile, skin, hair or other surfaces, so as to possibly remain on the substrate even after a rinsing step.

Among consumer products for which a high deposition is desired, one may cite rinse-off conditioners.

To address this specific problem, the use of cationic capsules is well-known.

For example, WO2009/153695 from the applicant discloses a simplified process for the preparation of polyurea microcapsules bearing permanent positive charges based on the use of a specific neutral emulsifier.

However, there is still a need to improve the ability of perfume delivery systems to deposit on a substrate and to adhere on the substrate for leave-on and rinse-off applications, while performing in terms of perfume release and stability.

The microcapsules of the invention solve this problem as they proved to show improvement in terms of deposition properties compared to what was known heretofore such as cationic delivery systems.

The present invention provides new microcapsules for delivering an encapsulated perfume and/or other hydrophobic materials, which combine the presence of an anionic emulsifier and a cationic polymer in a specific charge density ratio.

SUMMARY OF THE INVENTION

The present invention solves the above-mentioned problem by providing microcapsules with boosted deposition properties. It has been notably shown that cationic microcapsules having a positive zeta potential as the ones described in the prior art was not a sufficient condition to provide high deposition.

In particular, the inventors have underlined that the association of at least one cationic polymer with an anionic emulsifier in a particular charge ratio is unexpectedly tremendously improving the percentage of deposition of microcapsules on a substrate.

Indeed, the present invention now has determined a way to improve the efficiency in depositing microcapsules on a substrate in rinse-off applications. What is referred to as improving deposition or improving deposition efficiency is the percentage of microcapsules that remains on a substrate during use, in particular that remains on a substrate after a rinsing step. Better deposition translates then into an improvement in the delivery performance of the active ingredient encapsulated, for instance the olfactive performance in the case of a perfume, meaning that the microcapsules are able to deliver long lasting perception of a fragrance.

A first object of the invention is a core-shell microcapsule slurry comprising at least one microcapsule having
  a) an oil-based core;
  b) a polymeric shell formed by interfacial polymerisation in the presence of an anionic emulsifier; and
  c) a coating comprising at least one cationic polymer;
characterized in that:
  the charge ratio R(C/A) between the cationic polymer and the anionic emulsifier is between 2 and 3.5,
  the ratio between cationic polymer charge and polymeric shell weight R(C/S) is between 0.4 meq/g and 1.0 meq/g;
  the weight ratio between the cationic polymer and the anionic polymer is greater than 1.5, and
  the cationic polymer comprises a copolymer of acrylamidopropyltrimonium chloride and acrylamide
wherein $$R(C/A) = \frac{Q(\text{cationic polymer}) \times d(\text{cationic polymer})}{Q(\text{anionic emulsifier}) \times d(\text{anionic emulsifier})}$$

$$R(C/S) = \frac{Q(\text{cationic polymer}) \times d(\text{cationic polymer})}{m(\text{shell})}$$

wherein
Q(anionic emulsifier) is the quantity of anionic emulsifier in the slurry (g)
Q(cationic polymer) is the quantity of cationic polymer in the slurry (g)
d(anionic emulsifier) is the mean anionic charge density of anionic emulsifier at pH 9 (meq/g)
d(cationic polymer) is the mean cationic charge density of cationic polymer at pH 5 (meq/g) m (shell) is the weight of the polymeric shell (g)

A second object of the invention is a microcapsule powder obtained by drying the slurry as defined above.

A third object of the invention is a process for the preparation of a microcapsule slurry, comprising the following steps:
  a) Dissolving at least one monomer in an oil to form an oil phase;
  b) Preparing an aqueous solution of an anionic emulsifier to form a water phase;
  c) Adding the oil phase to the water phase to form an oil-in-water dispersion, wherein the mean droplet size is preferably comprised between 1 and 500 mm, more preferably between 3 and 50 mm;

d) Applying conditions sufficient to induce interfacial polymerisation and form microcapsules in form of a slurry;
wherein a step of adding at least one cationic polymer to form a cationic coating is carried out before or after step d),
characterized in that:
the ratio R(C/A) and the ratio R(C/S) are defined as above
the weight ratio between the cationic polymer and the anionic polymer is greater than 1.5, and
the cationic polymer comprises a copolymer of acrylamidopropyltrimonium chloride and acrylamide.

A fourth object of the invention is a perfuming composition comprising the microcapsule slurry or the microcapsule powder as defined above, wherein the core comprises a perfume.

A fifth object of the invention is a consumer product, preferably in the form of a rinse-off conditioner composition, a hair shampoo or a shower gel comprising the microcapsule slurry or the microcapsule powder or a perfuming composition as defined above.

A last object of the invention is the use of microcapsules as defined above for depositing microcapsules on a surface, preferably on hair and skin.

DETAILED DESCRIPTION OF THE INVENTION

Unless stated otherwise, percentages (%) are meant to designate a percentage by weight of a composition.

By "polyurea-based" wall or shell, it is meant that the polymer comprises urea linkages produced by either an amino-functional crosslinker or hydrolysis of isocyanate groups to produce amino groups capable of further reacting with isocyanate groups during interfacial polymerization.

By "polyurethane-based" wall or shell, it is meant that the polymer contains urethane linkages produced by reaction with polyols.

By "oil", it is meant an organic phase that is liquid at about 20° C. which forms the core of the core-shell capsules. According to any one of the invention embodiments, said oil comprises an ingredient or composition selected amongst a perfume, flavour, cosmetic ingredient, insecticide, malodour counteracting substance, bactericide, fungicide, insect repellent or attractant, drug, agrochemical ingredient and mixtures thereof.

By "perfume or flavour oil" also referred to as "perfume or flavour", it is meant a single perfuming or flavouring compound or a mixture of several perfuming or flavouring compounds.

For the sake of clarity, by the expression "dispersion" in the present invention it is meant a system in which particles are dispersed in a continuous phase of a different composition and it specifically includes a suspension or an emulsion.

By "mean charge density", it is meant the average number of charge by unit of polymer weight. For example, the mean charge density of sodium carboxymethyl cellulose refers to the moles of carboxylate functionalities (COO—) per gram of copolymer.

Charge density values of cationic polymers or anionic emulsifiers are available or can be determined by known experimental methods. When the molecular structure of the substance is known, the mean charge density can be calculated by the moles of proton or electron donors divided by the total molecular weight of the substance. One experimental method to obtain charge density is using mobility measurement by Malvern Zetasizer. From the mobility data measured, the polymer charge density can be calculated using the Ohshima's method, which relates the mobility of a soft particle to its charge density (D. Dong, Y. Hua, Y. Chen, X. Kong, C. Zhang, Q. Wang, *Journal of Agricultural and Food Chemistry*, 2013, 61, 3934-3940, V. Ducel, P. Saulnier, J. Richard, F. Boury, *Colloids and Surfaces B: Biointerfaces*, 2004, 95-102).

By "weight of the shell", it is meant the relative % wt of all materials that participate to form the shell. In the example of melamine glyoxal capsules, the shell is composed of guanozole, polyisocyanate (Takenate®), Melamine, Dimethoxyethanal, Glyoxal and Glyoxylic Acid. Materials added after the shell formation step, such as the cationic polymer coatings, pH adjusting acids, aldehyde scavengers and structuring agents, are not considered as being part of the capsule shell.

It has been found that the known effect of cationic polymer as a deposition aid for delivery systems could be significantly and unexpectedly enhanced when such cationic polymer was associated with the use of an anionic emulsifier in particular charge ratio.

Core-Shell Microcapsules Slurry

A first object of the invention is therefore a core-shell microcapsule slurry comprising at least one microcapsule having
  a) an oil-based core;
  b) a polymeric shell formed by interfacial polymerisation in the presence of an anionic emulsifier; and
  c) a coating comprising at least one cationic polymer;
characterized in that:
  the charge ratio R(C/A) between the cationic polymer and the anionic emulsifier is between 2 and 3.5,
  the ratio between cationic polymer charge and polymeric shell weight R(C/S) is between 0.4 meq/g and 1.0 meq/g,
  the weight ratio between the cationic polymer and the anionic polymer is greater than 1.5, and
  the cationic polymer comprises a copolymer of acrylamidopropyltrimonium chloride and acrylamide
wherein $$R(C/A) = \frac{Q(\text{cationic polymer}) \times d(\text{cationic polymer})}{Q(\text{anionic emulsifier}) \times d(\text{anionic emulsifier})}$$

$$R(C/S) = \frac{Q(\text{cationic polymer}) \times d(\text{cationic polymer})}{m(\text{shell})}$$

wherein
Q(anionic emulsifier) is the quantity of anionic emulsifier in the slurry (g)
Q(cationic polymer) is the quantity of cationic polymer in the slurry (g)
d(anionic emulsifier) is the mean anionic charge density of anionic emulsifier at pH 9 (meq/g)
d(cationic polymer) is the mean cationic charge density of cationic polymer at pH 5 (meq/g) m (shell) is the weight of the polymeric shell (g).

According to the invention, a single cationic polymer and/or a single anionic emulsifier can be used but a mixture of different cationic polymers and/or a mixture of different anionic emulsifiers can also be used. R(C/A) and R(C/S) can be defined therefore as follows:

$$R(C/A) = \frac{\sum_{i=1}^{n} [Q(\text{cationic polymer}) \times d(\text{cationic polymer})]}{\sum_{i=1}^{m} [Q(\text{anionic emulsifier}) \times d(\text{anionic emulsifier})]}$$

-continued $$R(C/S) = \frac{\sum_{i=1}^{n}[Q(\text{cationic polymer}) \times d(\text{cationic polymer})]}{m(\text{shell})}$$

Where n is the number of different cationic polymers, and
Where m is the number of different anionic emulsifiers.
According to an embodiment, m=1.
According to an embodiment, n>2.
According to a particular embodiment, n>2 and m=1.

A "core-shell microcapsule", or the similar, in the present invention is meant to designate a capsule that has a particle size distribution in the micron range (e.g. a mean diameter (d(v, 0.5)) comprised between about 1 and 3000 μm) and comprises an external solid oligomer-based shell or a polymeric shell and an internal continuous phase enclosed by the external shell.

The core-shell microcapsule according to the invention comprises an oil-based core. By "oil", it is meant an organic phase that is liquid at about 20° C. which forms the core of the core-shell capsules. According to any one of the invention embodiments, said oil comprises an ingredient or composition selected amongst a perfume, perfume ingredient, flavour, flavour ingredient, nutraceuticals, cosmetic ingredient, sunscreen agent, insecticide, malodour counteracting substance, bactericide, fungicide, biocide actives, insect repellent or attractant, insect control agent, drug, agrochemical ingredient and mixtures thereof.

According to a particular embodiment, said oil-based core comprises a perfume with another ingredient selected from the group consisting of nutraceuticals, cosmetics, insect control agents and biocide actives.

According to a particular embodiment, the oil-based core comprises a perfume or flavour. According to a preferred embodiment, the oil-based core comprises a perfume. According to another embodiment, the oil-based core consists of a perfume.

By "perfume oil" (or also "perfume") what is meant here is an ingredient or composition that is a liquid at about 20° C. According to any one of the above embodiments said perfume oil can be a perfuming ingredient alone or a mixture of ingredients in the form of a perfuming composition. As a "perfuming ingredient" it is meant here a compound, which is used for the primary purpose of conferring or modulating an odour. In other words such an ingredient, to be considered as being a perfuming one, must be recognized by a person skilled in the art as being able to at least impart or modify in a positive or pleasant way the odor of a composition, and not just as having an odor. For the purpose of the present invention, perfume oil also includes combination of perfuming ingredients with substances which together improve, enhance or modify the delivery of the perfuming ingredients, such as perfume precursors, emulsions or dispersions, as well as combinations which impart an additional benefit beyond that of modifying or imparting an odor, such as long-lasting, blooming, malodour counteraction, antimicrobial effect, microbial stability, insect control.

The nature and type of the perfuming ingredients present in the oil phase do not warrant a more detailed description here, which in any case would not be exhaustive, the skilled person being able to select them on the basis of its general knowledge and according to intended use or application and the desired organoleptic effect. In general terms, these perfuming ingredients belong to chemical classes as varied as alcohols, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said ingredients may also be compounds known to release in a controlled manner various types of perfuming compounds.

The perfuming ingredients may be dissolved in a solvent of current use in the perfume industry. The solvent is preferably not an alcohol. Examples of such solvents are diethyl phthalate, isopropyl myristate, Abalyn® (rosin resins, available from Eastman), benzyl benzoate, ethyl citrate, limonene or other terpenes, or isoparaffins. Preferably, the solvent is very hydrophobic and highly sterically hindered, like for example Abalyn® or benzyl benzoate. According to a particular embodiment, the solvent comprises low odour, high density materials like benzyl salicylate, cyclohexyl salicylate, hexyl salicylate. Preferably the perfume comprises less than 30% of solvent. More preferably the perfume comprises less than 20% and even more preferably less than 10% of solvent, all these percentages being defined by weight relative to the total weight of the perfume. Most preferably, the perfume is essentially free of solvent.

The nature of the polymeric shell of the microcapsules of the invention can vary. As non-limiting examples, the shell can be made of a polymeric material selected from the group consisting of polyurea, polyurethane, polyamide, polyacrylate, polysiloxane, polycarbonate, polysulfonamide, urea formaldehyde, melamine formaldehyde resin, melamine urea resin, melamine glyoxal resin, gelatin/gum arabic shell wall, and mixtures thereof.

The shell can also be hybrid, namely organic-inorganic such as a hybrid shell composed of at least two types of inorganic particles that are cross-linked, or yet a shell resulting from the hydrolysis and condensation reaction of a polyalkoxysilane macro-monomeric composition.

According to an embodiment, the shell comprises an aminoplast copolymer, such as melamine-formaldehyde or urea-formaldehyde or cross-linked melamine formaldehyde or melamine glyoxal.

Anionic Emulsifier

According to a particular embodiment, the anionic emulsifier has a mean charge density ranging from 0.5 and 4 meq/g, preferably from 0.7 to 4 meq/g, more preferably from 1 to 4 meq/g, even more preferably from 1 to 3 meq/g.

As non-limiting examples, the anionic emulsifier can be chosen in the group consisting of carboxymethyl modified cellulose, Gum Arabic, acrylate or methacrylate based polymers or copolymers and mixtures thereof.

According to a particular embodiment, the anionic emulsifier is sodium carboxymethylcellulose (anionic charge density=2.3 meq/g at pH=9).

Cationic Polymer

The microcapsule according to the invention is anionic before coating with the cationic polymer. The coating of such an anionic microcapsule with a cationic polymer is well-known from a skilled person in the art.

Microcapsules present in the particular composition of the invention are coated with at least one cationic polymer comprising a acrylamidopropyltrimonium chloride/acrylamide copolymer.

As specific examples of commercially available products, one may cite Salcare® SC60 (cationic copolymer of acrylamidopropyltrimonium chloride and acrylamide, origin: BASF).

In the present invention "poly(acrylamidopropyltrimonium chloride-co-acrylamide" and "acrylamidopropyltrimonium chloride/acrylamide copolymer" or "copolymer of acrylamidopropyltrimonium chloride and acrylamide" are used indifferently. According to a particular embodiment, microcapsules are coated with a mixture of at least two cationic polymers with the proviso that at least one cationic polymer is a acrylamidopropyltrimonium chloride/acrylamide copolymer. Such microcapsules are disclosed in WO 2017/001385 the content of which is also included by reference.

Cationic polymers are also well known to a person skilled in the art. Preferred cationic polymers have cationic charge densities of at least 0.5 meq/g, more preferably at least about 1.5 meq/g, but also preferably less than about 7 meq/g, more preferably less than about 6.2 meq/g. The cationic charge density of the cationic polymers may be determined by the Kjeldahl method as described in the US Pharmacopoeia under chemical tests for Nitrogen determination. The preferred cationic polymers are chosen from those that contain units comprising primary, secondary, tertiary and/or quaternary amine groups that can either form part of the main polymer chain or can be borne by a side substituent directly connected thereto. The weight average (Mw) molecular weight of the cationic polymer is preferably between 10,000 and 3.5M Dalton, more preferably between 50,000 and 2M Dalton.

According to a particular embodiment, one will use cationic polymers based on acrylamide, methacrylamide, N-vinylpyrrolidone, quaternized N,N-dimethylaminomethacrylate, diallyldimethylammonium chloride, quaternized vinylimidazole (3-methyl-1-vinyl-1H-imidazol-3-ium chloride), vinylpyrrolidone, acrylamidopropyltrimonium chloride, cassia hydroxypropyltrimonium chloride, guar hydroxypropyltrimonium chloride or polygalactomannan 2-hydroxypropyltrimethylammonium chloride ether, starch hydroxypropyltrimonium chloride and cellulose hydroxypropyltrimonium chloride. Preferably copolymers shall be selected from the group consisting of polyquaternium-5, polyquaternium-6, polyquaternium-7, polyquaternium10, polyquaternium-11, polyquaternium-16, polyquaternium-22, polyquaternium-28, polyquaternium-43, polyquaternium-44, polyquaternium-46, cassia hydroxypropyltrimonium chloride, guar hydroxypropyltrimonium chloride or polygalactomannan 2-hydroxypropyltrimethylammonium chloride ether, starch hydroxypropyltrimonium chloride and cellulose hydroxypropyltrimonium chloride As specific examples of commercially available products, one may cite Salcare® SC60 (cationic copolymer of acrylamidopropyltrimonium chloride and acrylamide, origin: BASF) or Luviquat®, such as the PQ 11N, FC 550 or Style (polyquaternium-11 to 68 or quaternized copolymers of vinylpyrrolidone origin: BASF), or also the Jaguar (C13S or C17, origin Rhodia).

According to any one of the above embodiments of the invention, there is added an amount of cationic polymer comprised between about 0.25 and 2.0 wt %, or even between about 0.5 and 1.5 wt %, percentage being expressed on a w/w basis relative to the total weight of the microcapsule slurry.

According to an embodiment, the cationic polymer has a charge density ranging from 0.5 to 4 meq/g, preferably from 0.7 to 3.2 meq/g.

As non-limiting examples, the cationic polymer can be chosen in the group consisting of poly(acrylamidoproyltrimonium chloride-co-acrylamide), copolymer of vinylpyrrolidone and quaternized vinylimidazol (Polyquaternium-44), polygalactomannan 2-hydroxy propyltrimethylammonium chloride ether or mixtures thereof.

According to a particular embodiment, the cationic polymer is chosen in the group consisting of a polygalactomannan selected from guar hydroxypropyltrimethylammonium chloride having a charge density from 0.5 to 2.0 meq/g, a acrylaminopropyltrimethylammonium chloride/acrylamide copolymer having a mean charge density from 1.5 to 2.5 meq/g, and mixtures thereof.

One may cite as commercial products:
Salcare® SC60 from BASF (poly(acrylamidoproyltrimonium chloride-co-acrylamide)) having a charge density of 1.9 meq/g at pH 5.
Jaguar C13S from Rhodia (polygalactomannan 2-hydroxy propyltrimethylammonium chloride ether) having a charge density of 0.8 meq/g at pH 5.
Luviquat® Ultra Care from BASF (Polyquaternium-44) having a charge density of 1 meq/g at pH 5.

According to a particular embodiment, the cationic coating comprises a mixture of poly(acrylamidoproyltrimonium chloride-co-acrylamide) and polygalactomannan 2-hydroxy propyltrimethylammonium chloride ether.

According to an embodiment, the charge ratio R(C/A) between the cationic polymer and the anionic emulsifier is between 2 and 3, preferably between 2 and 2.8 and/or the ratio between cationic polymer charge and polymeric shell weight R(C/S) is between 0.5 meq/g and 0.8 meq/g.

According to an embodiment, the total of cationic charge is comprised between 0.4 meq and 5 meq, preferably between 0.5 and 3, wherein the total of cationic charge is determined as follows:

$$\sum_{i=1}^{n} [Q(\text{cationic polymer}) \times d(\text{cationic polymer})]$$

wherein n is the number of the different cationic polymers.

According to an embodiment, the total of anionic charge is comprised between 0.2 meq and 2.5 meq, preferably between 0.25 and 1.5, wherein the total of anionic charge is determined as follows:

$$\sum_{i=1}^{m} [Q(\text{anionic polymer}) \times d(\text{anionic polymer})]$$

wherein m is the number of the different anionic emulsifiers.

According to the invention, the weight ratio between the cationic polymer and the anionic polymer is greater than 1.5, preferably greater than 2.0.

According to an embodiment, the weight ratio between the cationic polymer and the anionic polymer is comprised between 1.5 and 3.5, preferable between 2.0 and 3.5.

Microcapsule Powder

Another object of the invention is a microcapsule powder obtained by drying the slurry as defined above.

It is understood that any standard method known by a person skilled in the art to perform such drying is applicable.

In particular the slurry may be spray-dried preferably in the presence of a polymeric carrier material such as polyvinyl acetate, polyvinyl alcohol, dextrins, natural or modified starch, vegetable gums such as gum arabic, pectins, xanthans, alginates, carrageenans or cellulose derivatives to provide microcapsules in a powder form.

Process for Preparing Microcapsules

Another object of the present invention is a process for the preparation of microcapsule slurry as defined above, comprising the following steps:
a) Dissolving at least one monomer, in an oil to form an oil phase;
b) Preparing an aqueous solution of an anionic emulsifier to form a water phase;
c) Adding the oil phase to the water phase to form an oil-in-water dispersion, wherein the mean droplet size is preferably comprised between 1 and 500 μm, more preferably between 3 and 50 μm;
d) Applying conditions sufficient to induce interfacial polymerisation and form microcapsules in form of a slurry; and wherein a step of adding at least one cationic polymer to form a cationic coating is carried out before or after step d), characterized in that:
the ratios R(C/A) and R(C/S) are defined as previously
the weight ratio between the cationic polymer and the anionic polymer is greater than 1.5, and
the cationic polymer comprises acrylamidopropyltrimonium chloride/acrylamide copolymer.

According to a particular embodiment, the step of adding at least one cationic polymer is added after step d).

The process according to the present invention is characterized by the use of an anionic emulsifier in the preparation of the aqueous phase, which is used in combination with deposition-promoting material, in particular a cationic polymer according to specific charge ratio.

All components and features for the process are as defined above for the core-shell microcapsules.

The process according to the invention comprises the preparation of an oil phase by dissolving a polymer in an oil.

Depending on the nature of the microcapsule wall, the polymer can be chosen in the group consisting of a polyisocyanate having at least 2 isocyanate groups, the polyisocyanate being aromatic or aliphatic or mixtures thereof.

Preferably they contain at least three isocyanate groups. Following these numbers of functional groups, an optimal reticulation or network of the capsules wall is achieved, providing thus microcapsules exhibiting a prolonged slow release of fragrances, as well as a good stability in the consumer product.

Low volatility polyisocyanate molecules are preferred because of their low toxicity.

The term "aromatic polyisocyanate" is meant here as encompassing any polyisocyanate comprising an aromatic moiety. Preferably, it comprises a phenyl, a toluyl, a xylyl, a naphthyl or a diphenyl moiety, more preferably a toluyl or a xylyl moiety. Preferred aromatic polyisocyanates are biurets and polyisocyanurates, more preferably comprising one of the above-cited specific aromatic moieties. More preferably, the aromatic polyisocyanate is a polyisocyanurate of toluene diisocyanate (commercially available from Bayer under the tradename Desmodur® RC), a trimethylol propane-adduct of toluene diisocyanate (commercially available from Bayer under the tradename Desmodur® L75), a trimethylol propane-adduct of xylylene diisocyanate (commercially available from Mitsui Chemicals under the tradename Takenate® D-110N). According to a particular embodiment, the aromatic polyisocyanate is a trimethylol propane-adduct of xylylene diisocyanate.

The term "aliphatic polyisocyanate" is defined as a polyisocyanate which does not comprise any aromatic moiety. Preferred aliphatic polyisocyanates are a trimer of hexamethylene diisocyanate, a trimer of isophorone diisocyanate, a trimethylol propane-adduct of hexamethylene diisocyanate (available from Mitsui Chemicals) or a biuret of hexamethylene diisocyanate (commercially available from Bayer under the tradename Desmodur® N100), among which a biuret of hexamethylene diisocyanate is even more preferred.

According to any one of the invention embodiments, the oil contains a hydrophobic material selected from the group consisting of a perfume, flavour, cosmetic ingredient, insecticide, malodour counteracting substance, bactericide, fungicide, insect repellent or attractant, drug, agrochemical ingredient and mixtures thereof. According to a particular embodiment, the oil contains a perfume or flavour as defined above.

According to a preferred embodiment of the invention, there is used an amount of between 10 and 60%, more preferably between 20 and 50% of oil in the process of the invention, these percentages being defined by weight relative to the total weight of the obtained microcapsule slurry.

The process according to the present invention includes the use an anionic emulsifier in the preparation of the aqueous phase. Anionic emulsifier is preferably comprised in an amount ranging from 0.1 to 5.0% by weight of the microcapsule slurry, preferably between 1 and 2 wt % of the microcapsule slurry.

The capsules according to the present invention have a wall that is formed by interfacial polymerization. A skilled person in the art is well aware of various ways to induce interfacial polymerization.

According to an embodiment, the core-shell microcapsules are cross-linked melamine formaldehyde microcapsules and can be obtainable by a process comprising the steps of:
1) admixing a perfume oil with at least a polyisocyanate having at least two isocyanate functional groups to form an oil phase;
2) dispersing or dissolving into water an aminoplast resin and an anionic emulsifier to form a water phase;
3) adding the oil phase to the water phase to form an oil-in-water dispersion, wherein the mean droplet size is comprised preferably between 1 and 100 microns, by admixing the oil phase and the water phase;
4) performing a curing step to form the wall of said microcapsule;
5) adding at least one cationic polymer to the microcapsule slurry
6) optionally drying the final dispersion to obtain a dried core-shell microcapsule;

This process is described in more details in WO 2013/092375 and WO 2015/110568, the contents of which are included by reference.

According to a particular embodiment, the core-shell microcapsule is a formaldehyde-free capsule. A typical process for the preparation of aminoplast formaldehyde-free microcapsules slurry comprises the steps of:
1) preparing an oligomeric composition comprising the reaction product of, or obtainable by reacting together
   a) a polyamine component in the form of melamine or of a mixture of melamine and at least one $C_1$-$C_4$ compound comprising two $NH_2$ functional groups;

b) an aldehyde component in the form of a mixture of glyoxal, a $C_{4-6}$ 2,2-dialkoxy-ethanal and optionally a glyoxalate, said mixture having a molar ratio glyoxal/$C_{4-6}$ 2,2-dialkoxy-ethanal comprised between 1/1 and 10/1; and
c) a protic acid catalyst;
2) preparing an oil-in-water dispersion, wherein the droplet size is comprised between 1 and 600 um, and comprising:
 i. an oil;
 ii. a water medium containing an anionic emulsifier, preferably carboxymethylcellulose (Ambergum) or Gum Arabic an acrylate or methacrylate based polymer or copolymer,
 iii. at least an oligomeric composition as obtained in step 1;
 iv. at least a cross-linker selected amongst
 A) $C_4$-$C_{12}$ aromatic or aliphatic di- or tri-isocyanates and their biurets, triurets, trimmers, trimethylol propane-adduct and mixtures thereof; and/or
 B) a di- or tri-oxiran compounds of formula
 A-(oxiran-2-ylmethyl)$_n$
  wherein n stands for 2 or 3 and l represents a $C_2$-$C_6$ group optionally comprising from 2 to 6 nitrogen and/or oxygen atoms;
 v. optionally a $C_1$-$C_4$ compounds comprising two $NH_2$ functional groups;
3) heating said dispersion;
4) cooling said dispersion to form a capsule slurry, and
5) adding at least one cationic polymer to the capsule slurry.

This process is described in more details in WO 2013/068255, the content of which is included by reference.

According to another embodiment, the shell of the microcapsule is polyurea- or polyurethane-based. Examples of processes for the preparation of polyurea and polyurethane-based microcapsule slurry are for instance described in WO 2016/116604, the content of which is also included by reference.

Typically a process for the preparation of polyurea or polyurethane-based microcapsule slurry include the following steps:
a) dissolving at least one polyisocyanate having at least two isocyanate groups in an oil to form an oil phase;
b) preparing an aqueous solution of an anionic emulsifier or colloidal emulsifier to form a water phase;
c) adding the oil phase to the water phase to form an oil-in-water dispersion, wherein the mean droplet size is comprised between 1 and 500 µm, preferably between 3 and 50 µm;
d) applying conditions sufficient to induce interfacial polymerisation and form microcapsules in form of a slurry;
e) adding at least one cationic copolymer to the capsule slurry.

According to an embodiment, capsules according to the present invention are polyurea-based capsules. According to a particular embodiment, interfacial polymerization is induced by addition of a polyamine reactant. Preferably, the reactant is selected from the group consisting of water soluble guanidine salts and guanazole to form a polyurea wall with the polyisocyanate. According to another embodiment, polyurea-based capsules are formed in absence of added polyamine reactant, and result only from the autopolymerization of the at least one polyisocyanate, preferably in the presence of a catalyst. According to another embodiment, capsules according to the present invention are polyurethane-based capsules. According to this particular embodiment, interfacial polymerization is induced by addition of a polyol reactant. Preferably the reactant is selected from the group consisting of monomeric and polymeric polyols with multiple hydroxyl groups available for reaction and mixtures thereof.

According another embodiment, capsules according to the present invention are polyurea/polyurethane based. In that case interfacial polymerization is induced by addition of a mixture of the reactant mentioned under precedent first and second embodiments.

Additionally, crosslinkers with both amino groups and hydroxyl groups can be used to generate polyurea/polyurethane materials. Furthermore, polyisocyanates with both urea and urethane functionalities can be used to generate polyurea/polyurethane materials.

According to another embodiment, capsules according to the present invention are organic-inorganic hybrid capsules comprising inorganic particles.

Process conditions for interfacial polymerization do not need further description here as they are well known to a skilled person in the art.

The process according to the invention comprises the addition of a cationic polymer. Said polymer can be added any time after forming the dispersion. It can for example be added to the capsule slurry before or after crosslinking, when the capsule slurry is heated, or after it has cooled. The slurry conditions and pH can be optimized according to standard practice by a skilled person in the art. Suitable cationic polymers are mentioned above. The cationic polymer is preferably present in an amount comprised between 0.1 to 5% by weight of the microcapsule slurry, more preferably between 0.5 and 2% by weight of the microcapsule slurry.

According to a particular embodiment of the invention, the microcapsule slurry can be submitted to a drying, like spray-drying, to provide the microcapsules as such, i.e. in a powder form. It is understood that any standard method known by a person skilled in the art to perform such drying is applicable. In particular the slurry may be spray-dried preferably in the presence of a polymeric carrier material such as polyvinyl acetate, polyvinyl alcohol, dextrins, natural or modified starch, vegetable gums such as gum arabic, pectins, xanthans, alginates, carrageenans or cellulose derivatives to provide microcapsules in a powder form. Preferably, the carrier is a gum Arabic. According to one embodiment, the biopolymer used as emulsifier is also used as carrier material for further drying and the emulsifier or carrier also has the capacity to further encapsulate free perfume oil in addition to the microcapsules. According to a particular embodiment, the carrier material contains free perfume oil which can be same or different from the perfume from the core of the microcapsules.

Perfuming Composition and Consumer Products

A further object of the present invention is a perfuming composition comprising
(i) a microcapsule slurry or microcapsule powder as defined above, wherein the oil comprises a perfume; and
(ii) at least one ingredient selected from the group consisting of a perfumery carrier and a perfuming co-ingredient,
(iii) optionally a perfumery adjuvant.

As liquid perfumery carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery co-ingredient, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company). By "perfumery co-ingredient" it is meant here a compound, which is used in a perfuming preparation or a composition to impart a hedonic effect or modulate the overall odour and which is not a microcapsule as defined above. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the perfuming composition do not warrant a more detailed description here, which in any case would not be exhaustive, the skilled person being able to select them on the basis of his general knowledge and according to the intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

Preferably, the perfuming composition according to the invention comprises between 0.1 and 30% by weight of microcapsule slurry or microcapsule powder as defined above.

The invention's microcapsules can advantageously be used in all the fields of modern perfumery, i.e. fine or functional perfumery. Consequently, another object of the present invention is represented by a perfuming consumer product comprising as a perfuming ingredient, the microcapsules defined above or a perfuming composition as defined above.

The invention's microcapsules can therefore be added as such or as part of an invention's perfuming composition in a perfuming consumer product.

For the sake of clarity, it has to be mentioned that, by "perfuming consumer product" it is meant a consumer product which is expected to deliver at least a pleasant perfuming effect to the surface to which it is applied (e.g. skin, hair, textile, or home surface). In other words, a perfuming consumer product according to the invention is a perfumed consumer product which comprises a functional formulation, as well as optionally additional benefit agents, corresponding to the desired consumer product, e.g. a detergent or an air freshener, and an olfactive effective amount of at least one invention's compound.

The nature and type of the constituents of the perfumery consumer product do not warrant a more detailed description here, which in any case would not be exhaustive, the skilled person being able to select them on the basis of his general knowledge and according to the nature and the desired effect of said product. Formulations of consumer products in which the microcapsules of the invention can be incorporated can be found in the abundant literature relative to such products. These formulations do not warrant a detailed description here which would in any case not be exhaustive. The person skilled in the art of formulating such consumer products is perfectly able to select the suitable components on the basis of his general knowledge and of the available literature.

In particular, examples of such formulations can be found in handbooks such as for example Handbook of detergents; CTFA Cosmetic ingredient handbook, $10^{th}$ edition or more recent versions; Formulating detergents and personal care products: a guide to product development (2000); Cosmetic formulation of skin care products (2006) as well as in the abundant patent literature in the field of body care and home care consumer products.

Non-limiting examples of suitable perfumery consumer product include a perfume, such as a fine perfume, a cologne or an after-shave lotion; a fabric care product, such as a liquid or solid detergent, tablets and pods, a fabric softener, a dryer sheet, a fabric refresher, a liquid or solid perfumed booster (PEG or urea based pellets for example) an ironing water, or a bleach; a body-care product, such as a hair care product (e.g. a shampoo, leave-on or rinse-off hair conditioner, styling product, dry shampoo, a colouring preparation or a hair spray), a cosmetic preparation (e.g. a vanishing cream, body lotion or a deodorant or antiperspirant), or a skin-care product (e.g. a perfumed soap, shower or bath mousse, body wash, oil or gel, bath salts, shave gel or foam, cleansing wipes or a hygiene product); an air care product, such as an air freshener or a "ready to use" powdered air freshener; or a home care product, such all-purpose cleaners, liquid or power or tablet dishwashing products, toilet cleaners or products for cleaning various surfaces, for example sprays & wipes intended for the treatment/refreshment of textiles or hard surfaces (floors, tiles, stone-floors etc.). According to a preferred embodiment, the consumer product is a shampoo or a rinse-off conditioner. According to another preferred embodiment, the product is a perfumed soap. According to another preferred embodiment, the product is a body wash.

Preferably, the consumer product comprises from 0.1 to 15 wt %, more preferably between 0.2 and 5 wt % of the microcapsule slurry or microcapsule powder of the present invention, these percentages being defined by weight relative to the total weight of the consumer product. Of course the above concentrations may be adapted according to the olfactive effect desired in each product.

The capsules of the invention have proven to be particularly useful in rinse-off application as their deposition is much superior to delivery systems known heretofore.

Therefore, according to a particular embodiment, the consumer product is in the form of a rinse-off conditioner composition comprising:
  microcapsule slurry as defined above; and
  at least two components chosen in the list consisting of a non-quaternized conditioning ingredient, a water soluble cationic conditioning polymer and a quaternary ammonium salt.

Quaternary Ammonium Salts

Quaternary ammonium conditioning agents that can be used in the present invention are well known to those skilled in the art. Examples of such compounds are described in US2006/0210509 ([19] to [32]).

It has been found that a composition comprising a reduced amount of quaternary ammonium salts can be used to obtain a high deposition of microcapsules.

Thus, according to the invention, the composition comprises up to 4%, preferably up to 3%, more preferably up to 1.5% by weight of quaternary ammonium salts.

According to an embodiment, the composition comprises between 0 and 4 wt %, more preferably between 0 and 3 wt %, even more preferably between 0 and 1.5 wt % by weight of quaternary ammonium salts based on the total weigh of the composition.

According to another embodiment, the composition comprises between 0.01 and 4 wt %, more preferably between 0.01 and 3 wt %, even more preferably between 0.01 and 1.5 wt %, by weight of quaternary ammonium salts based on the total weigh of the composition.

According to a particular embodiment, the composition is free of quaternary ammonium salts.

Quaternary ammonium salts of the present invention are preferably quaternary ammonium salts bearing at least one long alkyl chain having between 10 carbons and 24 carbons. As non-limiting examples, one may cite behentrimonium chloride, cetrimonium chloride, behentrimonium methosulfate, ester-containing quaternary ammonium salts such as monoesterquats, diesterquats and triesterquats and mixtures thereof.

Surprisingly, it has been found that the partial or total substitution of quaternary ammonium salts with non-quarternized conditioning oils and optionally with water soluble cationic conditioning polymers and copolymers could improve the deposition of microcapsules.

Non-Quaternized Conditioning Ingredients

According to the invention, the non-quaternized conditioning ingredient is preferably hydrophobic or amphiphilic and comprises an oil or a wax or a mixture thereof.

According to an embodiment, the non-quaternized conditioning ingredient is chosen in the group consisting of an oil, a wax and mixture thereof.

According to the invention, the composition comprises between 0.25 and 15% by weight, preferably between 1 and 15%, more preferably between 3 and 15%, even more preferably between 5 and 15%, even more preferably between 6 and 15% by weight of non-quarternized conditioning ingredients based on the total weigh of the composition.

Non quaternized conditioning ingredients can be chosen from the group consisting of polysiloxanes, aminosiloxanes, dimethicone copolyols, alkyl silicone copolymers mineral oil, organic oils such as Macadamia oil, Jojoba oil, sunflower oil, almond oil, olive oil, fatty alcohols such as lanolin alcohol and cetearyl alcohol, fatty acids such as stearic acid, lauric acid, and palmitic acid, fatty acid esters, fatty acid amides such as Bis-Ethyl(Isostearylimidazoline) Isostereamide (Keradyn™ HH), bee wax, and mixtures thereof.

According to a particular embodiment, the non quaternized conditioning ingredient is chosen in the group consisting of stearate esters, cetearyl alcohol, jojoba oil, paraffin oil, bee wax, macadamia oil, lauric acid, olive oil, Bis-Ethyl (Isostearylimidazoline) Isostereamide, amodimethicone, dimethicone, and mixtures thereof.

According to an embodiment, the at least one non quaternized conditioning ingredient is a mixture between cetearyl alcohol and at least one component chosen in the group consisting of jojoba oil, paraffin oil, bee wax, macadamia oil, lauric acid, olive oil, Bis-Ethyl(Isostearylimidazoline) Isostereamide and mixtures thereof.

According to a particular embodiment, the non quaternized conditioning ingredient comprises Jojoba oil, preferably in combination with cetearyl alcohol.

According to another particular embodiment, the non quaternized conditioning ingredient comprises paraffin oil, preferably in combination with cetearyl alcohol.

According to another particular embodiment, the non quaternized conditioning ingredient comprises Bis-Ethyl (Isostearylimidazoline) Isostereamide (Keradyn™ HH), preferably in combination with cetearyl alcohol.

Water Soluble Cationic Conditioning Polymers

The composition of the invention can comprise water soluble cationic conditioning polymers and co-polymers preferably based on quarternized N,N-dimethylaminomethacrylate, diallyldimethylammonium chloride, quarternized vinylimidazole, vinylpyrrolidone, cassia hydroxypropyltrimonium chloride, guar hydroxypropyltrimonium chloride, polygalactomannan 2-hydroxypropyltrimonium chloride ether, starch hydroxypropyltrimonium chloride, cellulose hydroxypropyltrimoniumchloride, polyquaternium-5, polyquaternium-6, polyquaternium-7, polyquaternium-10, polyquaternium-11, polyquaternium-16, polyquaternium-22, polyquaternium-28, polyquaternium-43, polyquaternium-44, polyquaternium-46 and mixtures thereof and copolymers and terpolymers of the above with acrylic acid, methacrylic acid, acrylamide, methylacrylamide and N-vinylpyrrolidone.

The composition comprises less than 2%, preferably less than 1% of water soluble cationic conditioning polymers and co-polymers, preferably from 0.1 to 1% by weight based on the total weigh of the composition.

According to a particular embodiment, the composition is free of water soluble cationic conditioning polymers.

According to a particular embodiment, the composition comprises:
- from 0.1 to 5 wt % of a core-shell microcapsules slurry comprising microcapsules defined in the invention;
- up to 3 wt % by weight of at least one quaternary ammonium salt, preferably chosen in the group consisting of behentrimonium chloride, cetrimonium chloride, behentrimonium methosulfate, ester-containing quaternary ammonium salts such as monoesterquats, diesterquats and triesterquats and mixtures thereof;
- from 5 to 15%, preferably from 6 to 15 wt % by weight of at least one non quaternized conditioning ingredients, preferably chosen in the group consisting of stearate esters, cetearyl alcohol, jojoba oil, paraffin oil, bee wax, macadamia oil, lauric acid, olive oil, Bis-Ethyl(Isostearylimidazoline) Isostereamide, amodimethicone, dimethicone, and mixtures thereof;
- less than 1% by weight of water soluble cationic conditioning polymers, preferably chosen in the group consisting of Acrylamidopropyltrimonium Chloride/Acrylamide Copolymer, Guar Hydroxypropyltrimonium Chloride and mixture thereof; based on the total weight of the composition.

According to an embodiment, the composition of the invention is free of anionic, amphoteric or zwitterionic surfactants.

According to another embodiment, the consumer product is in the form of a hair shampoo or shower gel composition comprising:

- microcapsule slurry as defined above, preferably in an amount comprised between 0.05% and 5%, preferably between 0.2 and 5% by weight based on the total weight of the composition;
- at least one surfactant chosen from anionic and/or amphoteric surfactants, preferably in an amount comprised between 5 and 30% by weight based on the total weight of the composition Typical anionic surfactants include those surface active agents which contain an organic hydrophobic group with from 8 to 14 carbon atoms, preferably from 10 to 14 carbon atoms in their molecular structure; and at least one water-solubilising group which is preferably selected from sulphate, sulphonate, sarcosinate and isethionate. Specific examples of such anionic cleansing surfactants include ammonium lauryl sulphate, ammonium laureth sulphate, trimethylamine lauryl sulphate, trimethylamine laureth sulphate, triethanolamine lauryl sulphate, trimethylethanolamine laureth sulphate, monoethanolamine lauryl sulphate, monoethanolamine laureth sulphate, diethanolamine lauryl sulphate, diethanolamine laureth sulphate, lauric monoglyceride sodium sulphate, sodium lauryl sulphate, sodium laureth sulphate, potassium lauryl sulphate, potassium laureth sulphate, sodium lauryl sarcosinate, sodium lauroyi sarcosinate, lauryl sarcosine, ammonium cocoyi sulphate, ammonium lauroyi sulphate, sodium cocoyi sulphate, sodium lauryl sulphate, potassium cocoyi sulphate, potassium lauryl sulphate, monoethanolamine cocoyi sulphate, monoethanolamine lauryl sulphate, sodium tridecyl benzene sulphonate, sodium dodecyl benzene sulphonate, sodium cocoyi isethionate and mixtures thereof.

A preferred class of anionic cleansing surfactants for use in the invention are alkyl ether sulphates of general formula R—O—(CH$_2$CH$_3$—O)$_n$—SO$_3^-$M$^+$ in which R is a straight or branched chain alkyl group having 10 to 14 carbon atoms, n is a number that represents the average degree of ethoxylation and ranges from 1 to 5, preferably from 1 to 3, and M is a alkali metal, ammonium or alkanolammonium cation, preferably sodium, potassium, monoethanolammonium or triethanolammonium, or a mixture thereof.

Specific examples of such preferred anionic surfactants include the sodium, potassium, ammonium or ethanolamine salts of C10 to C12 alkyl sulphates and C10 to C12 alkyl ether sulphates (for example sodium lauryl ether sulphate), Mixtures of any of the above described materials may also be used.

In a typical composition according to the invention the level of anionic cleansing surfactant will generally range from 8 to 25%, and preferably ranges from 10 to 16% by weight based on the total weight of the composition.

The aqueous phase of the composition according to the invention preferably also includes one or more amphoteric surfactants, in addition to the anionic surfactant described above. Suitable amphoteric surfactants are betaines, such as those having the general formula R(CH$_3$)$^2$N$^+$CH2COO$^-$, where R is an alkyl or alkylamidoalkyl group, the alkyl group preferably having 10 to 16 carbon atoms. Particularly suitable betaines are oleyl betaine, caprylamidopropyl betaine, lauramidopropyl betaine, isostearylamidopropyl betaine, and cocoamidopropyl betaine. Cocoamidopropyl betaine is particularly preferred. When included, the total level of amphoteric surfactant is preferably from 0.1 to 10%, more preferably from 0.5 to 5%, and most preferably from 1 to 3% by weight based on the total weight of the composition).

The use of an anionic emulsifier and a cationic polymer according to specific charge ratios during the interfacial polymerisation and formation of the microcapsules is surprisingly significantly boosting the effect of the deposition promoting polymer. Therefore when microcapsules are applied on a substrate, the percentage of deposition is much higher than that of known systems as shown in the examples below. A method for improving deposition of microcapsules on a surface including but not limited to fabric, skin and hair, comprising treating said surface with a perfuming composition or a perfumed article comprising microcapsules as defined above is therefore also an object of the invention. Preferably the treated surface is hair or skin.

The invention will now be further described by way of examples. It will be appreciated that the invention as claimed is not intended to be limited in any way by these examples.

EXAMPLES

Deposition on Hair

For the following examples, the analytical deposition of microcapsules onto hair was measured as described below. Fragranced microcapsules were added to the rinse-off compositions at a dosage of 0.2% encapsulated perfume. The microcapsules contained perfume A described in Example 1, Table 1 and a UV tracer (Uvinul A Plus).

For the quantification of deposition, the following procedure was used. A 500 mg mini brown Caucasian hair swatch was wet with 40 mL of tap water (37° C.). The excess water was gently squeezed out once and 0.1 mL of the conditioner formulation containing microcapsules loaded with a UV tracer were applied. The conditioner was distributed for 30 seconds with gentle rubbing between two fingers. In order to copy a more realistic rinse procedure, the swatch was now dipped three times into a beaker filled with 200 ml of warm water followed by moving the swatch three times back and forward in the water. The procedure was repeated with a second beaker with 200 ml of fresh, warm water. The excess water was gently squeezed out and the hair swatch was then cut into a pre-weighed 20 mL scintillation vial. This process was repeated in triplicate and then the vials containing the cut hair were dried in a vacuum oven at 50-60° C. (100 Torr) for at least 5 hours.

After the drying process, the vials were again weighed to determine the mass of hair in the vials. Controls were also prepared by adding 0.1 mL of the rinse-off composition containing microcapsules to an empty vial. 8 mL of absolute ethanol were then added to each vial and they were subjected to 60 min of sonication. After sonication, the samples were filtered through a 0.45 µm PTFE filter and analysed with a HPLC using a UV detector. To determine the percentage of deposition of microcapsules from the conditioner compositions, the amount of Uvinul extracted from the hair samples was compared to the amount of Uvinul extracted from the control samples.

For each deposition measurement, 3 repeat hair swatch samples were prepared and the deposition value is reported as the average value of the three samples. In case, the variation between the depositions measured on each swatch was higher than 5%, another 3 samples were prepared.

Deposition on Skin

For the following examples, the analytical deposition of microcapsules onto skin was measured as described below.

Because human skin is not easily accessible to run a large number of deposition tests, a simplified method using glass plates has been developed.

Fragranced microcapsules were added to a shower gel composition at a dosage of 0.2% encapsulated perfume. The microcapsules contained perfume A described in Example 1, Table 1 and a UV tracer (Uvinul A Plus).

For the quantification of deposition, the following procedure was used. 1 g of the shower gel composition containing the microcapsules was diluted with 5 g of water. 50 mL of this dilution were distributed over a microscopic glass slide of 26 mm times 76 mm size. The glass slide was then rinsed with 10 ml of tap water (37° C.) three times on each side of the glass.

The rinsed glass slides were placed in a jar together with 20 ml of absolute ethanol and exposed to a controlled extraction process by placing the closed jars on a turbula mixer during 1 hour.

Controls were also prepared by adding 10, 25 and 50 mL of a 2% solution of capsules in water thickened by 2% hydroxypropyl cellulose, simulating a deposition of 20, 50 and 100%, to an empty vial. After the extraction, the samples were filtered through a 0.45 μm PTFE filter and analysed with a HPLC using a UV detector. To determine the percentage of deposition of microcapsules from the conditioner compositions, the amount of Uvinul extracted from the glass samples was compared to the amount of Uvinul extracted from the control samples.

For each deposition measurement, 6 repeat glass samples were prepared and the deposition value is reported as the average value of the six samples. A high deposition can be considered at measured values of 30% or above, ideally 40% or above.

Olfactive Performance

In some cases, the olfactive performance of microcapsules deposited on hair was tested in order to confirm the analytical deposition results by an olfactive intensity panel of 8 people. Fragranced microcapsules were added to the rinse-off compositions at a dosage of 0.2% encapsulated perfume. 10 g Caucasian brown hair swatches were used with a length of 20 cm and fixed with a flat metal clip. Caucasian hair, flat bundled, was chosen for this evaluation because Caucasian hair is rather thin in diameter and the application of viscous conditioner compositions can be guaranteed to be more reproducible compared to thick and course Asian hair. The hair swatches were rinsed with warm tap water (37° C.) and excess water was squeezed off manually. 1 g of the rinse-off product was applied on the swatch and distributed manually during 30 seconds, wearing nitrile gloves. The hair swatches were then rinsed under running tap water (37° C.) during 30 seconds while manually detangling the swatch. Excess water was manually squeezed off and swatches were air dried on a drying rack during 24 hours. Olfactive evaluation was carried out on the dried swatches by a group of 8 panelists. For each composition, two hair swatches were prepared. One remained un-combed and was smelled by each panelist for the value "before combing". The second swatch was combed by each panelist with a plastic comb three times to determine the value "after combing". Evaluation was carried out on coded samples and randomized. The intensity was reported on a scale from 1-7 (1=no odor, 7=maximum odor intensity). The average of 8 panelist evaluations is reported. As each panelist was combing 3 times, each swatch has been combed 24 times in total after the panel. This also allows to measure the use-up of the capsules during extended combing which is directly related to the amount of capsules deposited on the hair. A high performance of capsules can be considered of intensity values of 5 or above after combing.

Example 1

Preparation of Melamine Glyoxal Microcapsules Coated with Cationic Polymers

In a round bottom flask, melamine (0.87 g), 2,2-dimethoxyethanal (60 wt % in water, 1.37 g), glyoxal (40 wt % in water, 1.73 g) and glyoxylic acid (50 wt % in water, 0.58 g) were dispersed in water (1.48 g) at RT. The pH value of the dispersion was controlled with sodium hydroxide (30 wt % in water, pH=9.5). The reaction mixture was heated at 45° C. for 25 minutes to give a solution. Then water (6.31 g) was added and the resin was stirred at 45° C. for 5 min.

Resin was transferred in a 200 mL beaker. Guanazole (0.60 g) was dissolved in a solution of Ambergum 1221 (2 wt % in water, 27.04 g). The resulting solution was introduced into the beaker. An oil solution of Takenate D-110N (2.15 g), perfume A (28.06 g)—see table 1 and Uvinul A plus (1.41 g) was added into the aqueous solution. The biphasic reaction mixture was sheared with an Ultra-turrax at 21500 rpm for 2 min. Acetic acid was added to initiate the polycondensation (pH=5.35). The quality of the emulsion was controlled by light microscopy. The emulsion was transferred into a 200 mL Schmizo reactor and was heated at 45° C. for 1 h, then at 60° C. for 1 h and finally at 80° C. for 2 h. Varied amounts of a solution of first cationic copolymer namely acrylamidopropyltrimonium chloride/acrylamide copolymer (Salcare® SC60, origin BASF) (3 wt % in water), and second cationic copolymer polygalactomannan 2-hydroxy propyltrimethylammonium chloride ether (Jaguar C13S, origin Rhodia) (1 wt % in water), were then added and the reaction mixture was heated at 80° C. for 30 min. The specific amounts added for each cationic copolymer are specified in Table 2. A solution of urea (6.25 g, 50 wt % in water) was finally added to the reaction mixture, which was heated at 80° C. for 30 min.

The surface charge of the capsules was controlled by Zeta potential measurements (Nanosizer, Malvern). Each value was measured 3 times and the average value is stated. A positive Zeta potential indicated that the capsules were cationically charged.

TABLE 1

| Composition of perfume A | |
|---|---|
| Raw material | Qty (g) |
| Carbinol acetate | 2.20 |
| Citronellyl acetate | 16.59 |
| Linalyl acetate | 10.72 |
| Nopyle acetate | 7.97 |
| Terpinyl acetate | 2.11 |
| Verdyl acetate | 2.89 |
| Decanal | 0.07 |
| Hexylcinnamic aldehyde | 13.94 |
| Ethyl 2-methyl-pentanoate [1] | 0.26 |
| Benzyl benzoate | 8.19 |
| Cyclogalbanate | 2.14 |
| Hedione ® [2] | 11.94 |
| Hexyl isobutyrate | 2.63 |
| Nectalactone [3] | 10.34 |
| Oxane ® | 0.08 |
| Rose oxide | 0.44 |
| Verdyl propionate | 4.33 |
| Béta ionone | 0.52 |

TABLE 1-continued

Composition of perfume A

| Raw material | Qty (g) |
|---|---|
| Williams ester | 1.24 |
| 2,4-Dimethyl-3-cyclohexene-1-carbaldehyde [4] | 1.42 |

[1] Origin: Firmenich SA, Geneva, Switzerland
[2] Cyclopentaneacetic acid, 3-oxo-2-pentyl-, methyl ester; origin and trademark from Firmenich SA, Geneva, Switzerland
[3] (1'R)-2-[2-(4'-methyl-3'-cyclohexen-1'-yl)propyl]cyclopentanone (origin: Firmenich SA, Geneva, Switzerland)
[4] Origin: Firmenich SA, Geneva, Switzerland

TABLE 2

Melamine glyoxal microcapsules with different amount of cationic polymers

| Capsule | Perfume load in slurry | Salcare ® SC60 3% aqueous solution | Jaguar C13S 1% aqueous solution |
|---|---|---|---|
| Comparative 2-A | 35.95% | 0 g | 0 g |
| Comparative 2-B | 25.71% | 20.50 g | 10.50 g |
| Comparative 2-C | 22.53% | 30.75 g | 15.75 g |
| 2-E | 19.00% | 46.13 g | 23.63 g |
| 2-F | 18.05% | 51.25 g | 26.25 g |
| 2-G | 17.23% | 56.38 g | 28.63 g |
| 2-H | 16.42% | 61.50 g | 31.50 g |

TABLE 3

Cationic charge calculation for melamine glyoxal microcapsules

| Capsule | Salcare ® SC60 [1] (weight %) | Jagua C13S [2] (weight %) | total cationic change [3] (meq) |
|---|---|---|---|
| Comparative 2-A | 0 | 0 | 0.00 |
| Comparative 2-B | 0.56 | 0.1 | 1.14 |
| Comparative 2-C | 0.74 | 0.13 | 1.51 |
| 2-E | 0.93 | 0.16 | 1.90 |
| 2-F | 0.98 | 0.17 | 2.00 |
| 2-G | 1.03 | 0.17 | 2.09 |
| 2-H | 1.07 | 0.18 | 2.18 |

[1] copolymer of acrylamidopropyltrimonium chloride and acrylamide, origin: BASF (Salcare ® SC60 mean charge density: 1.9 meq/g)
[2] polygalactomannan 2-hydroxy propyltrimethylammonium chloride ether, origin Rhodia (Jaguar C13S mean charge density: 0.8 meq/g)
[3] Σ(wt % Salcare ® SC60 × 1.9 meq); (wt % Jaguar C13S × 0.8 meq)

TABLE 4

Shell weight and Anionic charge calculation for melamine glyoxal microcapsules

| Capsule | Shell [4] (weight %) S | Ambergum (weight %) | Anionic charge Ambergum [5] (meq) A |
|---|---|---|---|
| Comparative 2-A | 5.94 | 0.69 | 1.59 |
| Comparative 2-B | 4.25 | 0.50 | 1.15 |
| Comparative 2-C | 3.71 | 0.43 | 0.99 |
| 2-E | 3.14 | 0.37 | 0.85 |
| 2-F | 2.99 | 0.35 | 0.81 |
| 2-G | 2.85 | 0.33 | 0.76 |
| 2-H | 2.72 | 0.32 | 0.74 |

[4] wt % (Guanazole + Takenate + Melamine + Dimethoxyethanal + Glyoxal + Glyoxylic Acid added during shell polymerization)
[5] Carboxymethylcellulose, Ambergum mean charge density: 2.3 meq/g

TABLE 5

Calculated charge ratios for the melamine glyoxal microcapsules

| Capsule | r (C/S) [6] (meq/g) | r (C/A) [7] | Zeta potential average capsule slurry (V) | Std Dev |
|---|---|---|---|---|
| Comparative 2-A | 0.00 | 0.00 | −52.5 | 0.15 |
| Comparative 2-B | 0.27 | 0.99 | −38.0 | 1.41 |
| Comparative 2-C | 0.41 | 1.53 | −27.9 | 0.60 |
| 2-E | 0.60 | 2.23 | −1.5 | 0.31 |
| 2-F | 0.67 | 2.48 | +5.9 | 1.10 |
| 2-G | 0.73 | 2.76 | +18.1 | 1.32 |
| 2-H | 0.80 | 2.96 | +26.9 | 1.55 |

[6] cationic charge (Salcare ® SC60 + Jaguar C13S)/wt % shell (Guanazole + Takenate + Melamine + Dimethoxyethanal + Glyoxal + Glyoxylic Acid)
[7] Absolute value of cationic charge (Salcare ® SC60 + Jaguar C13S)/anionic charge (Ambergum)

By increasing the amount of cationic polymer coating, the perfume concentration in the slurry is decreasing (see table 2).

With no cationic polymer present, the capsule (2-A) is anionic with a Zeta potential of −52 mV. When the charge ratio between cationic coating and anionic emulsifier is close to 1, the resulting capsule charge still remains negative, indicating that further anionic charge is present in the capsule shell (2-B). At a charge ratio r(C/A) between 2 and 2.5, (2-E-2-F), the capsule charge becomes neutral with a Zeta potential near zero.

Example 2

Deposition of Melamine Glyoxal Microcapsules in Hair Rinse-Off Conditioners

The deposition of microcapsules in different rinse-off hair conditioners was measured on hair swatches.

The first conditioner composition was prepared as described below in Table 6. Three more conditioners were selected from commercial market product (see table 7). The capsules were post-added to the hair conditioner products at an equal dosage of encapsulated perfume of 0.2 wt %. The perfume contained 5% of Uvinul A Plus as a tracer to measure deposition of the microcapsules on hair.

TABLE 6

Hair rinse-off conditioner composition

| | Ingredients/INCI name | % |
|---|---|---|
| A | Water deionized | 81.8 |
| | Behentrimonium Chloride [1] | 2.5 |
| | Hydroxyethylcellulose [2] | 1.5 |
| B | Cetearyl Alcohol [3] | 4 |
| | Glyceryl Stearate (and) PEG-100 Stearate [4] | 2 |
| | Behentrimonium Methosulfate (and) Cetyl alcohol (and) Butylene Glycol [5] | 4 |
| | Ethoxy (20) Stearyl Alcohol [6] | 1 |
| C | Amodimethicone (and) Trideceth-12 (and) Cetrimonium Chloride [7] | 3 |
| | Chlorhexidine Digluconate [8] 20% aqueous solution | 0.2 |
| D | Citric acid 10% aqueous sol. till pH 3.5-4 | q.s. |
| | TOTAL: | 100 |

[1] Genamin KDMP, origin: Clariant
[2] Tylose H10 Y G4, origin: Shin Etsu
[3] Lanette O, origin: BASF
[4] Arlacel 165, origin: Croda
[5] Incroquat Behenyl TMS-50-PA-(MH), origin: Croda
[6] Brij S20, origin: Croda
[7] Xiameter MEM-949, origin: Dow Corning
[8] origin: Alfa Aesar Procedure:

1/Phase A: All ingredients were mixed until uniform; Tylose was allowed to completely dissolve. Then the Phase was heated up to 70-75° C.

2/Phase B: All ingredients were combined and melt at 70-75° C.

3/Phase B was added to Phase A (both at 70-75° C.) with good agitation. Mixing was continued until cooled down to 60° C.

4/Phase C was added while agitating and keeping mixing until the mixture cooled down to 40° C.

5/PH was adjusted with citric acid solution till pH: 3.5-4.0.

TABLE 7

Hair Rinse-off conditioner market products INCI list

| Dove Intense Repair Unilever, U.K. | Nivea, Volume Care Après Shampooing De Soin Avec extrait de bambo Cheveux fins ou plats Beiersdorf AG, Germany | PANTENE PRO-V Conditioner Daily Moisture Renewal Dreamcare Essential hydration from root to tip Procter and Gamble USA |
|---|---|---|
| Water | Water | Water |
| Cetearyl alcohol | Dimethicone | Stearyl Alcohol |
| Stearamidopropyl Dimethylamine | Stearyl Alcohol Cetyl Alcohol | Behentrimonium Methosulfate |
| Behentrimonium Chloride | Dimethicone Stearamidopropyl | Bis-Aminopropyl Dimethicone |
| Dimethicone (and) Amodimethicone (and) Cetrimonium Chloride | Dimethylamine Lanolin Alcohol (Eucerit ®) | Cetyl Alcohol Fragrance Benzyl Alcohol |
| Glycerine | Macadamia Ternifolia | Dicetyldimonium |
| Trehalose | Seed Oil | Chloride |
| Lactic Acid | Bambusa Vulgaris Shoot | Disodium EDTA |
| Adipic Acid | Extract | Histidine |
| Gluconalactone | Silicone Quaternium-18 | Panthenol |
| Disodium EDTA | Guar | Panthenyl Ethyl Ether |
| Sodium Chloride | Hydroxypropyltrimonium | Citric Acid |
| Sodium Sulphate | Chloride | Methylchloro- |
| PEG 7 Propylheptyl Ether | Lactic Acid Coco Betaine | isothiazolinone Yellow 5 |
| Fragrance | Trideceth-6 | Methylisothiazolinone |
| Dipropylene Glycol | C12-15 Pareth-3 | Red 33 |
| DMDM Hydantoin | Cocamidopropyl Betaine | |
| Phenoxyethanol | Citric Acid | |
| Alpha-Isomethyl Ionone | Propylene Glycol Potassium Sorbate | |
| Benzyl Alcohol | Phenoxyethanol | |
| Butylphenyl Mehylpropional | Ethylhexylglycerin Benzyl | |
| Hexyl Cinnamal | Alcohol | |
| Hydroxycitronellal | Citronellol | |
| Linalool | Fragrance | |

The ingredients in Table 7 are listed in the order as they appear on the packaging of the market products. This gives an indication on their relative concentration, as INCI directive demands to list the ingredients in the order of their relative concentration; highest concentration is listed first, lowest concentration is listed last.

TABLE 8

Deposition of melamine glyoxal microcapsules in rinse-off hair conditioners

Deposition measured on hair swatches in rel. wt % of capsules present in the applied rinse-off conditioner composition

| Capsules from Table 2 | r (C/A) [1] | Zeta potential (mV) | Rinse-off conditioner composition from Table 6 Deposition (%) | Std Dev | Dove Intense Repair Deposition (%) | Std Dev | Nivea, Volume Care Après Shampooing De Soin Deposition (%) | Std Dev | PANTENE PRO-V Conditioner Daily Moisture Renewal Dreamcare Deposition (%) | Std Dev |
|---|---|---|---|---|---|---|---|---|---|---|
| Comparative 2-A | 0.00 | −53 | 0.57% | 0.02 | 0.56% | 0.00 | 10.40% | 0.79 | 5.32% | 0.36 |
| Comparative 2-C | 1.53 | −28 | 8.89% | 0.77 | 3.15% | 0.58 | 11.12% | 1.36 | 6.53% | 1.14 |
| 2-F | 2.48 | +6 | 15.66% | 1.64 | 6.05% | 1.81 | 20.58% | 1.30 | 10.31% | 0.85 |
| 2G | 2.76 | +18 | 20.93% | 4.19 | 9.60% | 1.46 | 27.41% | 3.62 | 19.38% | 2.48 |

In order to confirm the analytical measurements, the capsules were also evaluated olfactively on larger hair swatches and the intensity, before and after combing, was noted by the panelists on a scale from 1 (no smell) to 7 (very intense smell).

TABLE 9

Fragrance intensity of melamine glyoxal microcapsules in rinse-off hair conditioners

| Capsules from Table 2 | r (C/A)[1] | Zeta potential (mV) | Rinse-off conditioner composition from Table 6 | Dove Intense Repair | PANTENE PRO-V Conditioner Daily Moisture Renewal Dreamcare |
|---|---|---|---|---|---|
| | | | Fragrance intensity before combing/ after combing on hair swatches washed with conditioners Intensity scale 1-7 | | |
| Comparative 2-A | 0 | −53 | 1.2/1.3 | 1.3/1.3 | 2.4/3.3 |
| 2-E | 2.23 | 4 | 3.6/5.4 | 2.0/4.8 | 3.0/5.2 |
| 2-F | 2.48 | 6 | 3.9/5.6 | 3.0/5.1 | 3.0/5.5 |
| 2-G | 2.76 | 18 | 4.1/6.3 | 2.6/6.4 | 3.3/5.7 |
| 2-H | 2.96 | 27 | 3.0/4.3 | 1.6/4.8 | 3.0/4.7 |

Conclusion

An increase in performance due to better deposition could be noticed with microcapsules of the present invention (Microcapsules 2E to 2H) compared to microcapsules outside of the invention (comparative 2A).

One can note that a significant increase in performance can be observed for microcapsules having a charge ratio r(C/A) between 2.2 and 2.8 (capsules 2E, 2F and 2G) whatever the nature of the rinse-off base.

Example 3

Deposition of Melamine Glyoxal Microcapsules in Hair Shampoos

Two shampoos, a transparent and a pearly one, were prepared and the deposition of microcapsules in these compositions was measured on hair swatches.

TABLE 10

Transparent hair shampoo composition

| | Transparent shampoo Ingredients/INCI name | % |
|---|---|---|
| A | Water deionized | 44.4 |
| | Polyquaternium-10 [1] | 0.3 |
| | Glycerin 85% [2] | 1 |
| | DMDM Hydantoin [3] | 0.2 |
| B | Sodium Laureth Sulfate [4] | 28 |
| | Cocamidopropyl Betaine [5] | 3.2 |
| | Disodium Cocoamphodiacetate [6] | 2 |
| C | Sodium Laureth Sulfate [4] | 4 |
| | Glyceryl Laureate [7] | 0.3 |
| D | Water deionized | 1 |
| | Sodium Methylparaben [8] | 0.1 |

TABLE 10-continued

Transparent hair shampoo composition

| | Transparent shampoo Ingredients/INCI name | % |
|---|---|---|
| E | Sodium Chloride 10% aqueous sol. | 15 |
| | Citric acid 10% aqueous sol. till pH 5.5-6 | q.s. |
| | Perfume | 0.5 |
| | TOTAL: | 100 |

[1] Ucare Polymer JR-400, origin: Noveon
[2] origin: Schweizerhall
[3] Glydant, origin: Lonza
[4] Texapon NSO IS (27% actives), origin: Cognis
[5] Tego Betain F 50 (38% actives), origin: Evonik
[6] Amphotensid GB 2009 (36% actives), origin: Zschimmer & Schwarz
[7] Monomuls 90 L-12, origin: Gruenau
[8] Nipagin Monosodium, origin: NIPA Procedure:
1/Phase A: The polymer JR-400 was dispersed in water. The remaining ingredients of Phase A were mixed separately by addition of one after the other while keep mixing.
2/Phase B and the premixed Phase C were added (Monomuls 90 L-12 was heated to melt in Texapon NSO IS) while agitating to mix.
3/Phase D and Phase E were added while agitating.
4/PH was adjusted with citric acid solution till pH: 5.5-6.0.

TABLE 11

Pearly hair shampoo composition

| | Pearly shampoo Ingredients/INCI name | % |
|---|---|---|
| A | Water deionized | 45.97 |
| | Tetrasodium EDTA [1] | 0.05 |
| | Guar Hydroxypropyltrimonium Chloride [2] | 0.05 |
| | Polyquaternium-10 [3] | 0.075 |
| B | NaOH 10% aqueous sol. | 0.3 |
| C | Ammonium Lauryl Sulfate [4] | 34 |
| | Ammonium Laureth Sulfate [5] | 9.25 |
| | Cocamidopropyl Betaine [6] | 2 |
| | Dimethicone (&) C12-13 Pareth-4 (&) C12-13 Pareth-23 (&) Salicylic Acid [7] | 2.5 |
| D | Cetyl Alcohol [8] | 1.2 |
| | Cocamide MEA [9] | 1.5 |
| | Glycol Distearate [10] | 2 |
| E | Methylchloroisothiazolinone & Methylisothiazolinone [11] | 0.1 |
| | D-Panthenol 75% [12] | 0.1 |
| | Water deionized | 0.3 |
| F | Sodium Chloride 25% aqueous sol. | 0.6 |
| | TOTAL: | 100 |

[1] EDETA B Powder, origin: BASF
[2] Jaguar C14 S, origin: Rhodia
[3] Ucare Polymer JR-400, origin: Noveon
[4] Sulfetal LA B-E, origin: Zschimmer & Schwarz
[5] Zetesol LA, origin: Zschimmer & Schwarz
[6] Tego Betain F 50, origin: Evonik
[7] Xiameter MEM-1691, origin: Dow Corning
[8] Lanette 16, origin: BASF
[9] Comperlan 100, origin: Cognis
[10] Cutina AGS, origin: Cognis
[11] Kathon CG, origin: Rohm & Haas
[12] D-Panthenol, origin: Roche Procedure:
1/Phase A: Jaguar C14 S and Ucare were added to water and EDETA while mixing.
2/Phase B: NaOH 10% solution was added once Phase A was homogeneous.
3/Phase C: Ingredients were added and mixture was heated to 75° C.

4/Phase D: Phase D ingredients were added and mixed till homogeneous and cooled down.

5/Phase E: At 45° C. Phase E were added while mixing.

6/Phase F: Final viscosity was adjusted with 25% NaCl solution and pH of 5.5-6 was adjusted with 10% NaOH solution.

TABLE 12

Deposition of melamine glyoxal microcapsules in hair shampoos

| | | | Deposition measured on hair swatches in rel. wt % of capsules present in the applied shampoo compositions | | | |
|---|---|---|---|---|---|---|
| | | | Transparent shampoo from Table 10 | | Pearly shampoo from Table 11 | |
| Capsules from Table 2 | r (C/A) [1] | Zeta potential (mV) | Deposition (%) | Std Dev | Deposition (%) | Std Dev |
| Comparative 2-A | 0 | −53 | 0.49% | 0.01 | 0.50% | 0.00 |
| 2-F | 2.48 | +6 | 28.20% | 6.05 | 14.02% | 2.58 |
| 2-G | 2.76 | +18 | 31.22% | 2.57 | 12.27% | 1.75 |
| 2-H | 2.96 | +27 | 21.62% | 3.96 | 11.45% | 2.48 |

TABLE 13

Fragrance intensity of melamine glyoxal microcapsules in hair shampoos

| | | | Fragrance intensity before combing/after combing on hair swatches washed with shampoos Intensity scale 1-7 | |
|---|---|---|---|---|
| Capsules from Table 2 | r (C/A) [1] | Zeta potential (mV) | Transparent shampoo from Table 10 | Pearly shampoo from Table 11 |
| Comparative 2-A | 0 | −53 | 1.5/1.5 | 1.3/1.4 |
| 2-E | 2.23 | −1.5 | 1.8/3.1 | 1.6/3.1 |
| 2-F | 2.48 | +6 | 2.6/3.3 | 2.0/2.8 |
| 2-G | 2.76 | +18 | 3.6/5.4 | 3.1/5.5 |
| 2-H | 2.96 | +27 | 2.2/4.6 | 2.0/2.6 |

[1] cationic charge (Salcare ® SC60 + Jaguar C13S)/anionic charge (Ambergum)

Conclusion

An increase in deposition could be noticed with microcapsules of the present invention (Microcapsules 2E to 2H) compared to microcapsules outside of the invention (comparative 2A).

One can note that a significant increase in deposition can be observed for microcapsules having a charge ratio r(C/A) between 2.4 and 3 (capsules 2F, 2G and 2H).

Example 4

Deposition of Melamine Glyoxal Microcapsules in Shower Gel

A structure, transparent shower gel was prepared and the deposition of microcapsules in these compositions was measured on microscopic glass plates.

TABLE 14

Structured shower gel composition

| Structured shower gel Ingredients/INCI name | % |
|---|---|
| Water deionized | 52.35 |
| Tetrasodium EDTA [1] | 0.05 |
| Acrylates Copolymer [2] | 6 |
| Sodium C12-C15 Pareth Sulfate [3] | 35 |
| Sodium Hydroxide 20% aqueous solution | 1 |
| Cocamidopropyl Betaine [4] | 5 |
| Methylchloroisothiazolinone and Methylisothiazolinone [5] | 0.1 |
| Citric Acid 40% aqueous sol. | 0.5 |
| TOTAL: | 100 |

[1] EDETA B POWDER; origin: BASF
[2] CARBOPOL AQUA SF-1 POLYMER; origin: NOVEON
[3] ZETESOL AO 328 U (26% actives); origin: ZSCHIMMER & SCHWARZ
[4] TEGO-BETAIN F 50 (38% actives); origin: GOLDSCHMIDT
[5] KATHON CG; origin: ROHM & HASS Procedure:

Ingredients were mixed in the given sequence.

pH was adjusted with 40% citric acid solution till pH 6.0-6.3

Viscosity: 4500 cPs+/−1500 cPs (Brookfield RV/Spindle #4/20 RPM)

TABLE 15

Deposition of melamine glyoxal microcapsules in structured shower gel

| | | Deposition measured on glass plates in rel. wt% of capsules present in the applied shower gel composition from Table 14 | |
|---|---|---|---|
| Capsules from Table 2 | r C/A [1] | Deposition (%) | Std Dev |
| Comparative 2-A | 0.00 | 0.00% | 0.00 |
| Comparative 2-C | 1.53 | 14.81% | 1.84 |
| 2-E | 2.23 | 44.99% | 6.54 |
| 2-F | 2.48 | 48.23% | 3.70 |
| 2-G | 2.76 | 41.79% | 3.10 |
| 2-H | 2.96 | 31.69% | 6.89 |

[1] cationic charge (Salcare ® SC60 + Jaguar C13S)/anionic charge (Ambergum)

Conclusion

Similar to the results obtained in shampoo on hair, microcapsules according to the invention show higher deposition than the comparative microcapsules.

Once again, the best deposition is obtained with microcapsules having a r(C/A) between 2 and 2.8.

Example 5

Preparation of Melamine Glyoxal Microcapsules with a Cationic Polymer Coating of Acrylamidopropyltrimonium Chloride/Acrylamide Copolymer Microcapsule 2-G from Example 1 was prepared with only using acrylamidopropyltrimonium chloride/acrylamide copolymer (Salcare® SC60) as the cationic coating but at the same total cationic charge as used in capsules 2G with a blend of acrylamidopropyltrimonium chloride/acrylamide copolymer (Salcare® SC60) and copolymer polygalactomannan 2-hydroxy propyltrimethylammonium chloride ether (Jaguar C13S).

In a round bottom flask, melamine (0.87 g), 2,2-dimethoxyethanal (60 wt % in water, 1.37 g), glyoxal (40 wt % in water, 1.66 g) and glyoxylic acid (50 wt % in water, 0.56 g) were dispersed in water (2.23 g) at RT. The pH value of the dispersion was controlled with sodium hydroxide (30 wt % in water, pH=9.5). The reaction mixture was heated at 45° C. for 25 minutes to give a solution. Then water (7.27 g) was added and the resin was stirred at 45° C. for 5 min.

Resin was transferred in a 200 mL beaker. Guanazole (0.59 g) was dissolved in a solution of Ambergum 1221 (2 wt % in water, 27.22 g). The resulting solution was introduced into the beaker. An oil solution of Takenate D-110N (2.10 g), perfume A from Table 1 (28.20 g) and Uvinul A plus (1.41 g) was added into the aqueous solution. The biphasic reaction mixture was sheared with an Ultra-turrax at 21500 rpm for 2 min. Acetic acid was added to initiate the polycondensation (pH=5.35). The quality of the emulsion was controlled by light microscopy. The emulsion was transferred into a 200 mL Schmizo reactor and was heated at 45° C. for 1 h, then at 60° C. for 1 h and finally at 80° C. for 2 h. An aqueous solution of acrylamidopropyltrimonium chloride/acrylamide copolymer (Salcare® SC60, origin BASF) 60.21 g, (3 wt % in water) was then added and the reaction mixture was heated at 80° C. for 30 min. A solution of urea (4.91 g, 50 wt % in water) was finally added to the reaction mixture, which was heated at 80° C. for 30 min.

The surface charge of the capsules was controlled by Zeta potential measurements (Nanosizer, Malvern). Each value was measured 3 times and the average value is stated. A positive Zeta potential indicated that the capsules were cationically charged.

TABLE 16

Melamine glyoxal microcapsules with Salcare ® SC60 copolymer

| Capsule | Perfume load in slurry | Salcare ® SC60 3% aqueous solution | Jaguar C13 S 1% aqueous solution |
|---|---|---|---|
| Comparative 2A | 35.95% | 0 g | 0 g |
| 15A | 17.18% | 60.21 g | 0 g |

TABLE 17

Cationic charge calculation for melamine glyoxal microcapsules

| Capsule | Salcare ® SC60 [1] (weight %) | Jaguar C13 S [2] (weight %) | total cationic charge [3] (meq) C |
|---|---|---|---|
| Comparative 2A | 0 | 0 | 0 |
| 15-A | 1.1 | 0 | 2.09 |

[1] Salcare ® SC60 charge density: 1.9 meq/g
[2] Jaguar C13S charge density: 0.8 meq/g
[3] Σ(wt % Salcare ® SC60 × 1.9 meq); (wt % Jaguar C13S × 0.8 meq)

TABLE 18

Shell weight and Anionic charge calculation for melamine glyoxal microcapsules

| Capsule | Shell [4] (weight %) S | Ambergum (weight %) | anionic charge Ambergum [5] (meq) A |
|---|---|---|---|
| Comparative 2A | 5.94 | 0.69 | 1.59 |
| 15A | 2.84 | 0.33 | 0.76 |

[4] wt % (Guanazole + Takenate + Melamine + Dimethoxyethanal + Glyoxal + Glyoxylic Acid added during shell polymerization)
[5] Ambergum charge density: 2.3 meq/g

TABLE 19

Calculated charge ratios for the melamine glyoxal microcapsules

| Capsule | r (C/S) [6] (meq/g) | r (C/A) [7] | Zeta potential average capsule slurry (mV) | Std Dev |
|---|---|---|---|---|
| Comparative 2A | 0 | 0 | −52.5 | 0.15 |
| 15A | 0.74 | 2.76 | +24.7 | 1.15 |

[6] cationic charge (Salcare ® SC60 + Jaguar C13S)/wt % shell (Guanazole + Takenate + Melamine + Dimethoxyethanal + Glyoxal + Glyoxylic Acid)
[7] cationic charge (Salcare ® SC60 + Jaguar C13S)/anionic charge (Ambergum)

Example 6

Deposition Performance of Melamine Glyoxal Microcapsules in Rinse-Off Applications (Hair Conditioners, Hair Shampoos and Shower Gel)

The deposition of the two microcapsules (comparative capsule 2A and 15A) was measured in different hair rinse-off products on hair swatches.

TABLE 20

Deposition of melamine glyoxal microcapsules in rinse-off hair conditioners

| Capsules | r (C/A) [1] | Zeta potential (mV) | Rinse-off conditioner composition from Table 6 Deposition (%) | Std Dev | Dove Intense Repair Deposition (%) | Std Dev | Nivea, Volume Care Après Shampooing De Soin Deposition (%) | Std Dev |
|---|---|---|---|---|---|---|---|---|
| Comparative 2-A | 0 | −53 | 0.57% | 0.02 | 0.56% | 0 | 10.40% | 0.79 |
| 15-A | 2.76 | 25 | 7.03% | 1.61 | 4.82% | 0.75 | 16.55% | 2.9 |

[1] cationic charge (Salcare ® SC60/anionic charge (Ambergum)

One can conclude from the table above that capsule 15A according to the invention shows a higher deposition than comparative capsules 2A.

In order to confirm the analytical measurements, the capsules were also evaluated olfactively on larger hair swatches and the intensity, before and after combing, was noted by the panelists on a scale from 1 (no smell) to 7 (very intense smell).

TABLE 21

Fragrance intensity of melamine glyoxal microcapsules in rinse-off hair conditioners Fragrance intensity before combing/after combing on hair swatches washed with conditioners Intensity scale 1-7

| Capsules | r (C/A) [1] | Zeta potential (mV) | Rinse-off conditioner composition from Table 6 | Dove Intense Repair | Nivea, Volume Care Après Shampooing De Soin | PANTENE PRO-V Conditioner Daily Moisture Renewal Dreamcare |
|---|---|---|---|---|---|---|
| Comparative 2-A | 0.00 | −53 | 1.2/1.3 | 1.3/1.3 | 2.9/4.8 | 2.4/3.3 |
| 15-A | 2.76 | +25 | 2.2/4.6 | 2.0/5.6 | 3.5/5.8 | 2.8/4.8 |

[1] cationic charge (Salcare ® SC60 + Jaguar C13S)/anionic charge (Ambergum)

TABLE 22

Deposition of melamine glyoxal microcapsules in hair shampoos

Deposition measured on hair swatches in rel. wt % of capsules present in the applied shampoo compositions

| Capsules | r (C/A) [1] | Zeta potential (mV) | Transparent shampoo from Table 10 Deposition (%) | Std Dev | Pearly shampoo from Table 11 Deposition (%) | Std Dev |
|---|---|---|---|---|---|---|
| Comparative 2-A | 0 | −53 | 0.49% | 0.01 | 0.50% | 0.00 |
| 15-A | 2.76 | +25 | 22.01% | 1.72 | 12.32% | 0.92 |

[1] cationic charge (Salcare ® SC60/anionic charge (Ambergum)

TABLE 23

Fragrance intensity of melamine glyoxal microcapsules in hair shampoos

Fragrance intensity before combing/after combing on hair swatches washed with shampoos Intensity scale 1-7

| Capsules from Table 2 | r (C/A) [1] | Zeta potential (mV) | Transparent shampoo from Table 10 | Pearly shampoo from Table 11 |
|---|---|---|---|---|
| Comparative 2-A | 0 | −53 | 1.5/1.5 | 1.3/1.4 |
| 15-A | 2.76 | +25 | 2.3/4.8 | 2.0/3.7 |

The deposition of the two microcapsules was measured in the structured shower gel from Table 14 on glass plates.

TABLE 24

Deposition of melamine glyoxal microcapsules in shower gel

| Capsules | r C/A) [1] | Zeta potential (mV) | deposition measured on glass plates in rel. wt % of capsules present in the applied shower gel composition from Table 14 | |
|---|---|---|---|---|
| | | | Deposition (%) | Std Dev |
| Comparative 2-A | 0.00 | −53 | 0.00% | 0.00 |
| 15-A | 2.76 | +25 | 34.33% | 3.02 |

Conclusion

In all rinse-off conditioners tested as well as in the transparent shampoo base and in the structured shower gel, the capsule which was only coated with Salcare® SC60 copolymer (15-A) provided a better deposition than the comparative microcapsule 2A.

Example 7

Synthesis of Polyurea Microcapsules with Cationic Polymer Coating—Capsules Outside the Invention The capsules were prepared in a one litre glass double-jacked reactor equipped with a scrapped stirrer and with an Ystral-rotor/stator system (500-1800 rpm).

In a typical experiment, 5.1 g of polyisocyanate (Desmodur® N100, origin: Bayer) were dissolved in 40 g of perfume. This oil phase was introduced in the reactor and stirred with the scrapped stirrer at 50 rpm.

The aqueous emulsifier solution was prepared by dissolving the polyvinyl alcohol (Mowiol® 18-88, origin: Fluka) and a selected concentration of the cationic copolymers Luviquat® Ultra Care (polyquaternium-44, origin: BASF), Salcare® SC60 (acrylamidopropyltrimonium chloride/acrylamide copolymer, origin: BASF) and Jaguar C13S (polygalactomannan 2-hydroxy propyltrimethylammonium chloride, origin Rhodia) in deionized water. The final concentration of the polyvinyl alcohol was 0.3% in the total weight of the emulsifier solution and the concentration of the cationic copolymers varied as listed in Table 5.

54.9 g of the emulsifier solution were introduced into the reactor at room temperature. The scrapped stirrer was stopped and then a pre-emulsion was prepared by dispersion the perfume phase into the aqueous phase by using a rotor/stator system. Once the emulsion was prepared, the stirring was continued with the scrapped stirrer at 200 rpm till the end of the process. Then, a solution of 0.9 g of guanidine carbonate (origin: Fluka) in 2.4 g deionized water was added to the reactor in 6 times (every 10 minutes) at room temperature. During one hour the temperature of the reaction mixture was then slowly increased up to 70° C. and kept at 70° C. for another two hours. The stirring speed was then decreased to 100 rpm and the capsule suspension was cooled down to room temperature.

TABLE 25

Polyurea microcapsules with different amount of cationic copolymers

| Capsule | Perfume load in slurry | Luviquat® Ultra Care [1] weight % | Salcare® SC60 [2] weight % | Jaguar C13 S [3] weight % | total cationic charge via copolymers C [4] (meq) |
|---|---|---|---|---|---|
| 23-A | 38.50% | 0% | 0% | 0% | 0 |
| 23-B | 38.50% | 0.34% | 0% | 0% | 0.34 |
| 23-C | 38.50% | 0.43% | 0% | 0% | 0.43 |
| 23-D | 38.50% | 0.57% | 0% | 0% | 0.57 |
| 23-E | 38.50% | 0% | 0.26% | 0.04% | 0.53 |
| 23-F | 38.50% | 0% | 0.34% | 0.06% | 0.69 |
| 23-G | 38.50% | 0% | 0.42% | 0.07% | 0.85 |
| 23-H | 38.50% | 0% | 0.60% | 0.10% | 1.22 |

[1] charge density: 1.0 meq/g
[2] charge density: 1.9 meq/g
[3] charge density: 0.8 meq/g
[4] Σ(amount copolymer × charge density)

TABLE 26

Zeta potential measured of original vs. filtered polyurea microcapsules from Table 25

| Capsule | total cationic charge via copolymers C [4] (meq) | r (C/S) [5] (meq/g) | Zeta potential average (mV) | Std Dev |
|---|---|---|---|---|
| 23-A | 0 | 0.00 | −5.5 | 0.76 |
| 23-B | 0.34 | 0.07 | +4.9 | 0.42 |
| 23-C | 0.43 | 0.09 | +7.0 | 0.26 |
| 23-D | 0.57 | 0.12 | +19.0 | 1.78 |
| 23-E | 0.53 | 0.11 | +23.7 | 2.08 |
| 23-F | 0.69 | 0.14 | +32.7 | 0.58 |
| 23-G | 0.85 | 0.18 | +21.7 | 0.58 |
| 23-H | 1.22 | 0.25 | +33.9 | 1.75 |

[4] Σ(amount cationic copolymer * charge density)
[5] cationic charge (Luviquat + Salcare ® SC60 + Jaguar C13S)/relative amount of shell material (Takenate + Polyvinyl Alcohol + Guanidine Carbonate)

Conclusion

The surface charge of the capsules was controlled by Zeta potential measurements (Nanosizer, Malvern). A positive Zeta potential indicated that the capsules were cationically charged. Due to the absence of anionic emulsifiers in the composition, the capsules are positively charged at any amount of cationic copolymer added.

Example 8

Deposition of Polyurea Microcapsules Outside of the Invention in Hair Shampoos and Rinse-Off Hair Conditioners Polyurea microcapsules were applied in a rinse-off conditioner and in a shampoo, which showed highest deposition with the melamine glyoxal microcapsules and deposition was measured on hair swatches.

We will complete the table with NIVEA ROC and Transparent Shampoo base.

TABLE 27

Deposition of polyurea microcapsules in shampoos and rinse-off conditioners

| Capsules from Table 23 | total cationic charge via copolymers C [4)] (meq) | Cationic copolymers used | Deposition in transparent Shampoo from Table 10 | Nivea, Volume Care Après Shampooing De Soin Avec extrait de bambou Cheveux fins ou plats Beiersdorf AG, Germany |
|---|---|---|---|---|
| 23-A | 0 | Luviquat ® Ultra Care [1)] | 0.00% | 0.40% |
| 23-B | 0.34 | Luviquat ® Ultra Care [1)] | 0.00% | 0.33% |
| 23-C | 0.43 | Luviquat ® Ultra Care [1)] | 0.00% | 0.39% |
| 23-D | 0.57 | Luviquat ® Ultra Care [1)] | 0.00% | 0.71% |
| 23-E | 0.53 | Salcare ® SC60 [2)] Jaguar C13 S [3)] | 0.73% | 0.58% |
| 23-F | 0.69 | Salcare ® SC60 [2)] Jaguar C13 S [3)] | 0.67% | 0.67% |
| 23-G | 0.85 | Salcare ® SC60 [2)] Jaguar C13 S [3)] | 0.69% | 0.48% |
| 23-H | 1.22 | Salcare ® SC60 [2)] Jaguar C13 S [3)] | 0.67% | 0.47% |

[1)] Polyquaternium-44, BASF
[2)] Poly(acrylamidoproyltrimonium chloride-co-acrylamide), BASF
[3)] polygalactomannan 2-hydroxy propyltrimethylammonium chloride ether, Rhodia Conclusion One can conclude from this table that Capsules 23-A to 23-H (outside of the invention with a r (C/S)<0.5) show a very poor deposition in all rinse-off products tested, independent on the amount or type of the cationic copolymer coating. This example shows that having a high zeta potential is not enough to induce high capsule deposition.

Example 9

Synthesis of Polyurea Microcapsules with Anionic Emulsifier and Cationic Polymer Coating A solution of Superstab™ AA (Gum Arabic, Hercules Inc.) in water (1.85 wt %, 55 g) was added in a beaker of 100 mL. A solution of perfume oil (Table 1) (38.00 g), Uvinul® A+(oil soluble UVA filter, Bayer) (2.00 g), and polyisocyanate-Takenate® D-110N ((75%) (trimethylol propane adduct of xylylene diisocyanate, trademark from: Mitsui Chemicals) (5 . . . 10 g)—was added into the beaker and both phases were sheared with UltraTurrax at 24000 rpm for 2 min. The emulsion was transferred into a 250 mL reactor and heat at 45° C. for 1 h, then at 60° C. for 1 h, and finally at 80° C. for 2 h. Aqueous solutions of cationic copolymer of acrylamidopropyltrimonium chloride and acrylamide (Salcare® SC60, origin: BASF) (3 wt %) and of a second cationic copolymer polygalactomannan 2-hydroxy propyltrimethylammonium chloride ether (Jaguar C13S, origin Rhodia) (1 wt % in water) were added and the dispersion was stirred at 80° C. for 1 h. The reaction mixture was finally cooled down to RT (pH=3.80). The specific amounts added for each cationic copolymer are specified in Table 28.

TABLE 28

Polyurea microcapsules with different amount of cationic polymers

| Capsule | Perfume load in slurry | Salcare ® SC60 [1)] 3% aqueous solution | Jaguar C13 S [2)] 1% aqueous solution |
|---|---|---|---|
| 26-E | 27.99% | 28.60 g | 14.30 g |
| 26-F | 21.99% | 54.60 g | 27.30 g |

[1)] cationic copolymer of acrylamidopropyltrimonium chloride and acrylamide (Salcare ® SC60 ® SC60, origin: BASF)
[2)] cationic copolymer polygalactomannan 2-hydroxy propyltrimethylammonium chloride ether (Jaguar C13S, origin Rhodia)

TABLE 29

Cationic charge calculation for polyurea microcapsules

| Capsule | Salcare ® SC60 [1)] (weight %) | Jaguar C13 S [2)] (weight %) | total cationic charge [3)] (meq) C |
|---|---|---|---|
| 26-E | 0.6 | 0.1 | 1.22 |
| 26-F | 0.9 | 0.15 | 1.83 |

[1)] Salcare ® SC60 charge density: 1.9 meq/g
[2)] Jaguar C13S charge density: 0.8 meq/g
[3)] Σ(wt % Salcare ® SC60 × 1.9 meq); (wt % Jaguar C13S × 0.8 meq)

TABLE 30

Shell weight and Anionic charge calculation for polyurea microcapsules

| Capsule | Shell w/o Superstab AA [4)] (weight %) S | Superstab AA (weight %) | anionic charge Superstab AA [5)] (meq) A |
|---|---|---|---|
| 26-E | 2.68 | 0.70 | 0.7 |
| 26-F | 2.1 | 0.55 | 0.55 |

[4)] wt % Takenate
[5)] Superstab AA charge density: 1.0 meq/g

TABLE 31

Calculated charge ratios for the polyurea microcapsules and Zeta potentials

| Capsule | r (C/S) [6)] (meq/g) | r (C/A) [7)] | C + A | Zeta potential average capsule slurry (mV) | Std Dev |
|---|---|---|---|---|---|
| 26-F | 0.87 | 3.33 | 1.28 | 43.0 | 0.92 |

[6)] cationic charge (Salcare ® SC60 + Jaguar C13S)/wt % shell (Takenate)
[7)] cationic charge (Salcare ® SC60 + Jaguar C13S)/anionic charge Superstab AA

Example 10

Deposition of Polyurea Microcapsules with Anionic Emulsifier and Cationic Polymer Coating in Hair Shampoos and Rinse-Off Hair Conditioners Polyurea microcapsules were applied in a transparent shampoo (see composition in Table 10), and deposition was measured on hair swatches.

Microcapsule deposition was measured on hair swatches and is given in rd. wt % of capsules present in a transparent shampoo.

TABLE 32

Deposition of poyurea microcapsules in transparent hair shampoo

| Capsule | Salcare ® SC60 [1] (weight %) | C13 S [2] (weight %) | r (C/A) [3] | Zeta potential average capsule slurry (mV) | Tranparent Shampoo from Table 10 Deposition (%) | Std Dev |
|---|---|---|---|---|---|---|
| 26-F | 0.9 | 0.15 | 3.33 | +43.0 | 18.26% | 2.22 |

[1] cationic copolymer of acrylamidopropyltrimonium chloride and acrylamide (Salcare ® SC60, origin: BASF)
[2] cationic copolymer polygalactomannan 2-hydroxy propyltrimethylammonium chloride ether (Jaguar C13S, origin Rhodia)
[3] cationic charge (Salcare ® SC60 + Jaguar C13S)/anionic charge Superstab AA)

Conclusion

Polyurea microcapsules comprising an anionic emulsifier and cationic polymers according to the range claimed in the present invention show good performance in terms of deposition in a shampoo composition.

The invention claimed is:

1. A core-shell microcapsule slurry comprising at least one microcapsule having
   a) an oil-based core;
   b) a polymeric shell formed by interfacial polymerisation in the presence of an anionic emulsifier; and
   c) a coating comprising at least one cationic polymer;
   wherein:
   a charge ratio R(C/A) between the cationic polymer and the anionic emulsifier is between 2 and 3.5,
   a ratio between cationic polymer charge and polymeric shell weight R(C/S) is between 0.4 meq/g and 1.0 meq/g,
   a weight ratio between the cationic polymer and the anionic emulsifier is greater than 1.5, and
   the cationic polymer comprises a copolymer of acrylamidopropyltrimonium chloride and acrylamide;
   wherein $$R(C/A) = \frac{Q(\text{cationic polymer}) \times d(\text{cationic polymer})}{Q(\text{anionic emulisifier}) \times d(\text{anionic emulsifier})}$$

$$R(C/S) = \frac{Q(\text{cationic polymer}) \times d(\text{cationic polymer})}{m(\text{shell})}$$

wherein
Q(anionic emulsifier) is a quantity of anionic emulsifier in the slurry (g)
Q(cationic polymer) is a quantity of cationic polymer in the slurry (g)
d(anionic emulsifier) is a mean anionic charge density of anionic emulsifier at pH 9 (meq/g)
d(cationic polymer) is a mean cationic charge density of cationic polymer at pH 5 (meq/g)
m (shell) is a weight of the polymeric shell (g).

2. The slurry according to claim 1, wherein:
   the charge ratio R(C/A) between the cationic polymer and the anionic emulsifier is between 2 and 3, and/or
   the ratio between cationic polymer charge and polymeric shell weight R(C/S) is between 0.5 meq/g and 0.8 meq/g.

3. The slurry according to claim 2, wherein:
   the charge ratio R(C/A) between the cationic polymer and the anionic emulsifier is between 2 and 2.8 and/or
   the ratio between cationic polymer charge and polymeric shell weight R(C/S) is between 0.5 meq/g and 0.8 meq/g.

4. The slurry according to claim 1, wherein the anionic emulsifier has a mean charge density ranging from 1 to 4 meq/g.

5. The slurry according to claim 4, wherein the anionic emulsifier is selected from the group consisting of modified carboxymethyl cellulose, Gum Arabic, acrylate or methacrylate based polymers or copolymers, and mixtures thereof.

6. The slurry according to claim 4, wherein the anionic emulsifier has a mean charge density ranging from 2 to 3 meq/g.

7. The slurry according to claim 1, wherein the cationic polymer has a mean charge density ranging from 1 to 4 meq/g.

8. The slurry according to claim 7, wherein the cationic polymer is a mixture of a guar hydroxypropyltrimethylammonium chloride having a mean charge density from 0.5 to 2.0 meq/g and a acrylaminopropyltrimethylammonium chloride/acrylamide copolymer having a mean charge density from 1.5 to 2.5 meq/g.

9. The slurry according to claim 7, wherein the cationic polymer has a mean charge density ranging from 2 to 3 meq/g.

10. The slurry according to claim 1, wherein the oil comprises a perfume.

11. A perfuming composition comprising
    (i) perfume microcapsules slurry as defined in claim 7;
    (ii) at least one ingredient selected from the group consisting of a perfumery carrier and a perfuming co-ingredient; and
    (iii) optionally a perfumery adjuvant.

12. The slurry according to claim 1, wherein the polymeric shell is made of a material selected from the group consisting of polyurea, polyurethane, polyamide, polyacrylate, polysiloxane, polycarbonate, polysulfonamide, urea formaldehyde, melamine formaldehyde resin, melamine urea resin, melamine glyoxal resin, gelatin/gum arabic shell wall and mixtures thereof.

13. A microcapsule powder obtained by drying the slurry as defined in claim 1.

14. A consumer product, in the form of a home- or personal-care product, comprising microcapsule slurry as defined in claim 1.

15. A consumer product according to claim 14, in the form of a rinse-off conditioner composition comprising:
    at least two components chosen in the list consisting of a non-quaternized conditioning ingredient, a water soluble cationic conditioning polymer and a quaternary ammonium salt.

16. A consumer product according to claim 14, in the form of a hair shampoo or shower gel composition comprising:

at least one surfactant chosen from anionic or amphoteric surfactants.

17. A process for the preparation of a microcapsule slurry, comprising the following steps:
   a) Dissolving at least one monomer in an oil to form an oil phase;
   b) Preparing an aqueous solution of an anionic emulsifier to form a water phase;
   c) Adding the oil phase to the water phase to form an oil-in-water dispersion;
   d) Applying conditions sufficient to induce interfacial polymerisation and form microcapsules in form of a slurry; and
      wherein a step of adding at least one cationic polymer is carried out before or after step d) to form a cationic coating,
   wherein:
   the charge ratio R(C/A) between the cationic polymer and the anionic emulsifier is between 2 and 3.5,
   the ratio between cationic polymer charge and polymeric shell weight R(C/S) is between 0.4 meq/g and 1 meq/g
   the weight ratio between the cationic polymer and the anionic emulsifier is greater than 1.5, and
   the cationic polymer comprises a copolymer of acrylamidopropyltrimonium chloride and acrylamide,
   wherein $$R(C/A) = \frac{Q(\text{cationic polymer}) \times d(\text{cationic polymer})}{Q(\text{anionic emulsifier}) \times d(\text{anionic emulsifier})}$$

$$R(C/S) = \frac{Q(\text{cationic polymer}) \times d(\text{cationic polymer})}{m(\text{shell})}$$

wherein
Q(anionic emulsifier) is the quantity of anionic emulsifier in the slurry (g)
Q(cationic polymer) is the quantity of cationic polymer in the slurry (g)
d(anionic emulsifier) is the charge density of anionic emulsifier at pH 9 (meq/g)
d(cationic polymer) is the charge density of cationic polymer at pH 5 (meq/g)
m (shell) is the weight of the polymeric shell (g).

18. The process according to claim 17, wherein it comprises the steps of:
   a) admixing a perfume oil with at least a polyisocyanate having at least two isocyanate functional groups to form an oil phase;
   b) dispersing or dissolving into water an aminoplast resin and an anionic emulsifier to form a water phase;
   c) adding the oil phase to the water phase to form an oil-in-water dispersion by admixing the oil phase and the water phase;
   d) performing a curing step to form the wall of said microcapsule; and
   wherein a step of adding at least one cationic polymer is carried out before or after step d) to form a cationic coating,
   wherein R(C/A) and R(C/S) are as defined in claim 17.

19. The process according to claim 17, wherein a mean droplet size of the oil-in-water dispersion is between 1 and 500 mm.

20. The process according to claim 17, wherein a mean droplet size of the oil-in-water dispersion is between 3 and 50 mm.

* * * * *